(12) United States Patent
Rasmussen et al.

(10) Patent No.: US 7,084,247 B2
(45) Date of Patent: Aug. 1, 2006

(54) IDENTIFICATION OF SELF AND NON-SELF ANTIGENS IMPLICATED IN AUTOIMMUNE DISEASES

(75) Inventors: James Rasmussen, Cambridge, MA (US); Bei Yu, West Roxbury, MA (US)

(73) Assignee: Peptimmune, Inc., Cambridge, MA (US)

(*) Notice: Subject to any disclaimer, the term of this patent is extended or adjusted under 35 U.S.C. 154(b) by 0 days.

(21) Appl. No.: 10/799,005

(22) Filed: Mar. 11, 2004

(65) Prior Publication Data

US 2005/0202034 A1 Sep. 15, 2005

(51) Int. Cl.
*A61K 38/04* (2006.01)

(52) U.S. Cl. .................... 530/326; 514/2; 424/185.1
(58) Field of Classification Search .............. 514/2; 424/185.1
See application file for complete search history.

(56) References Cited

U.S. PATENT DOCUMENTS

| 5,130,297 A | 7/1992 | Sharma et al. |
| 5,194,425 A | 3/1993 | Sharma et al. |
| 5,874,531 A | 2/1999 | Strominger et al. |

FOREIGN PATENT DOCUMENTS

| WO | WO 90/08161 | 7/1990 |
| WO | WO 92/16234 | 10/1992 |
| WO | WO 92/18150 | 10/1992 |
| WO | WO 93/10813 | 6/1993 |
| WO | WO 94/05303 | 3/1994 |
| WO | WO 94/06828 | 3/1994 |
| WO | WO 95/12313 | 5/1995 |

OTHER PUBLICATIONS

Veldman et al., "T cell recognition of desmoglein 3 peptides in patients with pemphigus vulgaris and healthy individuals" Journal of Immunology, 2004, 172:3883-3892.*
Goon et al., "Pemphigus vulgaris following varicella infection" Clinical and Experimental Dermatology, 2001, 26:661-663.*
Vanderlugt and Miller, "Epitope spreading in immune-mediated diseases: implications for immunotherapy" Nature Reviews Immunology, 2002, 2:85-95.*
Wucherpfenning et al., "Structural basis for MHC-linked susceptibility to autoimmunity: Charged residues of a single MHC binding pocket confer selective presentation of self-peptides in pemphigus vulgaris" Proc. Natl. Acad. Sci. USA 1995 92:11935-11939.*
Veldman et al., "Dichotomy of autoreactive Th1 and Th2 cell responses to desmoglein 3 in patients with pemphigus vulgaris (PV) and helthy carriers of PV-associated HLA Class II alleles" J. Immunol. 2003, 170:635-642.*
Ahmed, A. R., Yunis, E. J., Khatri, K., Wagner, R., Notani, G., Awdeh, Z., & Alper, C. A. (1990). Major histocompatibility complex haplotype studies in Ashkenazi Jewish patients with Pemphigus vulgaris. Proc. Natl. Acad. Sci. (USA) 87: 7658.
Ahmed, A. R., Wagner, R., Khatri, K., Notani, G., Awdeh, Z., and Yunis, E. J. (1991). "Major histocompatibility complex haplotypes and class II genes in non-Jewish patients with Pemphigus vulgaris." Proc. Natl. Acad. Sci. (USA) 88: 5056.
Alexander, J. et al., "Functional Consequences of Engagement of the T Cell Receptor by Low Affinity Ligands," J. Immunol., 150(1): 1-7 (1993).
Allegretta, M., Nicklas, J. A., Sriram, S. and Albertini, R. J. (1990). "T cells responsive to myelin basic protein in patients with multiple sclerosis." Science 247: 718-721.
Amagai, M., Klaus-Kovtun, V., & Stanley, J. R. (1991). "Autoantibodies against a novel epithelial cadherin in Pemphigus vulgaris, a disease of cell adhesion." Cell 67:869-877.
Amagai, M., Karpati, S., Prussick, R., Klaus-Kovtun, V., & Stanley, J. R. (1992). "Autoantibodies against the amino-terminal cadherin-like binding domain of Pemphigus vulgaris antigen are pathogenic." J. Clin. Invest. 90:919.

(Continued)

*Primary Examiner*—Christina Chan
*Assistant Examiner*—Michael Szperka
(74) *Attorney, Agent, or Firm*—Fish & Neave IP Group Ropes & Gray LLP

(57) ABSTRACT

The present invention provides isolated peptides relating to the autoimmune disease pemphigus vulgaris. The peptides relating to pemphigus vulgaris are self epitopes derived from human pathogens which are implicated in the aetiology and remissions of the disease. Pharmaceutical preparations for tolerizing and/or immunizing individuals are provided as well as methods relating thereto. Methods are provided for identifying other self and non-self epitopes involved in human autoimmune disease and similar pharmaceutical preparations and methods of use for these epitopes are also provided.

12 Claims, No Drawings

OTHER PUBLICATIONS

Bankier et al., "Sequence Analysis for the 17, 166 Base-pair EcoRI fragment C of B95-8 Epstein-Barr Virus." Mol. Biol. Med. 1: 21-45 (1983).

Brewerton, D. A., Hart, F. D., Caffrey, M., Nicholls, A., James, D. C. O., & Sturrock, R. D. (1973). "Ankylosing spondylitis and HL-A 27." Lancet 1: 904.

Brown, J. H., Jardetzky, T. S., Gorga, J. C., Stern, L. J., Urban, R. G., Strominger, J. L., & Wiley, D. C. (1993). "Three-dimensional structure of the human class II histocompatibility antigen HLA-DR1." Nature 364: 33.

Brown, L.R. et al., "Recognition of the influenza hemaglutinin by class II MHC-restricted T lymphocytes and antibodies, I. Site definition and implications for antigen presentation and T lymphocyte recognition." J. Immunol., 147(8):2677-2684 (1991).

Busch, R., Hill, C. M., Hayball, J. D., Lamb, J. R., Rothbard, J. B. (1991). "Effect of a natural polymorphism at residue 86 of the HLA-DR .beta. chain on peptide binding." J. Immunol. 147:1292-1298.

Chambers et al., "Antigenic and Molecular Characterization of Subtype H13 Hemagglutinin of Influenza Virus." Virology 172: 180-188 (1989).

Chicz, R. M., Urban, R. G., Gorga, J. C., Vignali, D. A. A., Lane, W. S., & Strominger, J. L. (1993). "Specificity and promiscuity among naturally processed peptides bound to HLA-DR alleles." J. Exp. Med. 178:27.

Chicz, R. Et al., "Predominant naturally processed peptides bound to HLA-DR1 are derived from MHC-related molecules and are heterogeneous in size." Nature, 358: 764-768 (1992).

Datta, A. K., Feighny, R. J., Pagano, J. S. (1980). "Induction of Epstein-Barr virus-associated DNA polymerase by 12-O-tetradecanoylphorbol-13-acetate." J. Biol. Chem. 255: 5120-5125.

Dermody et al., "The S2 Gene Nucleotide Sequences of Prototype Strains of the Three Reovirus Serotypes: Characterization of Reovirus Core Protein o2." J. of Virology 65(11): 5721-5721 (1991).

Epstein, M. A., Achong, B. G. (1977). "Pathogenesis of infectious mononucleosis." Lancet 11: 1270-1272.

Gregersen, P. K., Silver, J., Winchester, R. J. (1987). "The shared epitope hypothesis. An approach to understanding the molecular genetics of susceptibility to rheumatoid arthritis." Arthritis Rheum. 30: 1205-1213.

Hammer, J. et al., "Promiscuous and Allele-Specific Anchors in HLA-DR Binding Peptides." Cell, 74: 197-203 (1993).

Hogenkamp et al., "Nucleotide Sequence of the Right 10% of Adenovirus Type 12 DNA Encoding the Entire Region E4." Nucleic Acids Research 18(10): 3065-3066 (1990).

Jardetzky, T. S., Lane, W. S., Robinson, R. A., Madden, D. R., & Wiley, D. C. (1991). "Identification of self-peptides bound to purified HLA-B27." Nature 353: 326.

Jardetzky, T. S. et al., "Peptide binding to HLA-DR1: a peptide with most residues substituted to alanine retains MHC binding." EMBO J., 9(6): 1797-1803 (1990).

Johnson, R. T., Griffin, D. E., Hirsch, J. S., Wolinsky, J. S., Rodenbeck, S., Lindo De Soriano, I. and Vaisberg, A. (1984). "Measles encephalomyelitis. Clinical and immunological studies." N. Engl. J. Med. 310: 137-141.

Kaufman, D. L., Clare-Salzler, M., Tian, J., Forsthuber, T., Ting, G. S. P., Robinson, P., Atkinson, M. A., Sercarz, E. E., Tobin, A. J., and Lehmann, P. V. (1993). "Spontaneous loss of T-cell tolerance to glutamic acid decarboxylase in murine insulin-dependent diabetes." Nature 366: 69-72.

Kurtzke, J. F. (1985). "Epidemiology of multiple sclerosis" in Handbook of clinical neurology Eds. P. J. Vinken, G. W. Bruyn, H. L. Klawans and J. C. Koetsier. Amsterdam/New York, Elsevier Sci. 259-287.

Lanchbury, J. S., & Panayi, G. S. (1991). "Genetics of RA: the HLA shared epitope hypothesis and its implications." Br. J. Rheumatol. 30(Suppl 2): 6.

Lehmann, P. V., Forsthuber, T., Miller, A. and Sercarz, E. E. (1992). "Spreading of T-cell autoimmunity to cryptic determinants of an autoantigen." Nature 358: 155-157.

Madden, D. R., Gorga, J. C., Strominger, J. L., & Wiley, D. C. (1991). "The structure of HLA-B27 reveals nonamer self-peptides bound in an extended conformation." Nature 353: 321.

Madden, D.R. et al., "The Antigenic Identity of Peptide-MHC Complexes: A Comparison of the Conformation of Five Viral Peptides Presented by HLA-A2." Cell, 75:693-708 (1993).

Marsh, S. G. E. and Bodmer, J. G. (1992). "HLA class II nucleotide sequences, 1992." Human Immunol. 35: 1-17.

Martin, R., Jaraquemada, D., Flerlage, M., Richert, J., Whitaker, J., Long, E. O., McFarlin, D. E. and McFarland, H. F. (1990). "Fine specificity and HLA restriction of myelin basic protein-specific cytotoxic T cell lines from multiple sclerosis patients and healthy individuals." J. Immunol. 145: 540-548.

McGeoch et al., "DNA sequence of the region in the genome of herpes simplex virus type 1 containing excinuclease gene and neighbouring genes." Nucleic Acid Research, 14(8): 1434-1448 (1986).

O'Sullivan, D. et al., "On The Interaction of Promiscuous Antigenic Peptides With Different DR Alleles; Identification of common structural motifs." J. Immunol., 147(8): 2663-2669 (1991).

Oldstone, M. B. A. (1990). "Molecular mimicry and autoimmune disease." Cell 50: 819-820.

Olerup, O., Hillert, J., Fredrickson, S., Olsson, T., Kam-Hansen, S., Moeller, E., Carlsson, B. and Wallin, J. (1989). "Primary chronic progressive and relapsing/remitting multiple sclerosis: Two immunogenetically distinct disease entities." Proc. Natl. Acad. Sci. (USA) 86:7113-7117.

Oltersdorf et al., "Molecular Cloning and Characterization of Human Papillomavirus Type 7 DNA." Virology, 149: 247-250 (1986).

Ota, K., Matsui, M., Milford, E. L., Mackin, G. A., Weiner, H. L. and Hafler, D. A. (1990). "T-cell recognition of an immunodominant myelin basic protein epitope in multiple sclerosis." Nature 346: 183-187.

Pette, M., Fujita, K., Wilkinson, D., Altmann, D. M., Trowsdale, J., Giegerich, G., Hinkkanen, A., Epplen, J. T., Kappos, L. and Wekerle, H. (1990). "Myelin autoreactivity in multiple sclerosis: Recognition of myelin basic protein in the context of HLA-DR2 products by T lymphocytes of multiple sclerosis patients and healthy donors." Proc. Natl. Acad. Sci. (USA) 87: 7968-7972.

Protti, M. P., Manfredi, A. A., Horton, R. M., Bellone, M., Conti-Tronconi, B. M. (1993). "Myasthenia gravis: recognition of a human autoantigen at the molecular level." Immunol. Today 14: 363.

Ray, C. G., Palmer, J. P., Crossley, J. R. and Williams, R. H. (1980). "Coxsackie B virus antibody responses in juvenile-onset diabetes mellitus." Clin. Endocrinol. (Oxf) 12: 375-378.

Reay, P. et al., "Use of Global Amino Acid Replacements to Define the Requirements for MHC Binding and T Cell Recognition of Moth Cytochrome c (93-103)." J. Immunol., 150: 3946-3957 (1994).

Rose, N. R., Wolfgram, L. J., Herskowitz, A. and Beisel, K. W. (1986). "Postinfectious autoimmunity: Two distinct phases of coxsackie B3-induced myocarditis." Ann. N.Y. Acad. Sci. 475: 146-156.

Rotschke, O., & Falk, K. (1991). "Naturally-occuring peptide antigens derived from the MHC class-I-restricted processing pathway." Immunol. Today 12: 447.

Rotschke, O. et al., "Origin, Structure and Motifs of Naturally Processed MHC Class II Ligands." Current Opinion Immunol., 6: 45-51 (1994).

Scharf, S. J., Long, C. M., & Erlich, H. A. (1988). "Sequence analysis of the HLA-DR.beta. and DQ.beta. loci from three Pemphigus vulgaris patients." Human Immunol. 22: 61.

Schlosstein, L., Terasaki, P. I., Bluestone, R., & Pearson, C. M. (1973). "High association of an HL-A antigen, W27, with ankylosing spondylitis." N. Enql. J. Med. 288: 704.

Schwarz, E., Freese, U. K., Gissman, L., Mayer, W., Roggenbuck, B., Stremlau, A., zur Hausen, H. (1985). "Structure and transcription of human papillomavirus sequences in cervical carcinoma cells." Nature 314: 111-114.

Sinha, A. A., Brautbar, C., Szafer, F., Friedmann, A., Tzfoni, E., Todd, J. A., Steinman, L., & McDevitt, H. O. (1988). "A newly characterized HLA-DQ.beta. allele associated with Pemphigus vulgaris." Science 239: 1026-1029.

Sloan-Lancaster, J., Evavold, B. D., and Allen, P. M. (1993) "Induction of T-cell anergy by altered T-cell-receptor ligand on live antigen-presenting cells." Nature 363: 156-159.

Sloan-Lancaster, J., Shaw, A. S., Rothbard, J. B. and Allen, P. M. (1994). "Partial T cell signalling: Altered Phospho-.zeta. and lack of Zap70 recruitment in APL-induced T cell anergy." Cell 79: 913-922.

Spielman, R. S., & Nathenson, N. (1982). "The genetics of susceptibility to multiple sclerosis." Epidemol. Rev. 4: 45.

Spruance, S. (1985). "Pathogenesis of herpes simplex labialis: Experimental induction of lesions with UV light." J. Clin. Microbiol. 22: 366-368.

Steinman, L. "Escape from 'Horror Autotoxicus': Pathogenesis and Treatment of Autoimmune Disease." Cell, 80(1): 7-10 (1995).

Stern, L. J., Brown, J. H., Jardetzky, T. S., Urban, R., Strominger, J. L., & Wiley, D. C. (1994). "Crystal structure of the human class II MHC protein HLA-DR1 complexed with an influenza virus peptide." Nature 368: 215.

Takeichi, M. (1990). "Cadherins: A molecular family important in selective cell—cell adhesion." Ann. Rev. Biochem. 59: 237.

Tian, J., Lehmann, P. V. and Kaufman, D. L. (1994). "T cell cross- reactivity between coxsackievairus and glutamate decarboxylase is associated with a murine diabetes susceptibility allele." J. Exp. Med. 180: 1979-1984.

Tisch, R., Yang, X.-D., Singer, S. M., Liblau, R. S., Fugger, L., and McDevitt, H. O. (1993). "Immune response to glutamic acid decarboxylase correlates with insulitis in non-obese diabetic mice." Nature 366: 72-75.

Todd, J. A., Bell, J. I., & McDevitt, H. O. (1987). "HLA-DQ.beta. gene contributes to susceptibility and resistance to insulin-dependent diabetes mellitus." Nature 329: 599.

Tovey, M. G., Lenoir, G. and Begon-Lours, J. (1978). "Activation of latent Epstein-Barr virus by antibody to human IgM," Nature 276: 270-272.

Tsurumi et al. "A Single-Base Change Within the DNA Polymerase Locus and Herpes Simplex Virus Tepy 2 Can Confer Resistance to Aphidicolin." J. of Virology, 61(2): 388-394 (1987).

Vogt, A. B., Kropshofer, H., Kalbacher, H., Kalbus, M., Rammensee, H.-G., Coligan, J. E. and Martin, R. (1994). "Ligand motifs of HLA-DRB5*0101 and DRB1*1501 molecules delineated from self-peptides." J. Immunol. 151: 1665-1673.

Wucherpfennig, K. W., Sette, A., Southwood, S., Oseroff, C., Matsui, M., Strominger, J. L. and Hafler, D. A. (1994a). "Structural requirements for binding of an immunodominant myelin basic protein peptide to DR2 isotypes and for its recognition by human T cell clones." J. Exp. Med. 179: 279-290.

Wucherpfennig, K. W., Zhang, J., Witek, C., Matsui, M., Modabber, Y., Ota, K. and Hafler, D. A. (1994b). "Clonal expansion and persistence of human T cells specific for an immunodominant myelin basic protein peptide." J. Immunol. 150: 5581-5592.

Wucherpfennig, K. et al., "T-cell recognition of myelin basic protein," Immunol. Today, 12(8): 277-282 (1991).

Zamvil, S. S. and Steinman, L. (1990). "The T lymphocyte in experimental allergic encephalomyelitis." Annual Rev. Immunol. 8: 579-621.

Zhang, J., Markovic, S., Lacet, B., Raus, J., Weiner, H. L. and Hafler, D. A. (1994). "Increased frequency of interleukin 2-responsive T cells specific for myelin basic protein and proteolipid protein in peripheral blood and cerebrospinal fluid of patients with multiple sclerosis." J. Exp. Med. 179: 973-984.

Zielinski et al., "Characterization and Regulation of the *Pseudomonas aeroginosa* algC Gene Encoding Phophomannomutase." J. Biol. Chem., 266(15): 9754-9762 (1991).

Loiseau Pascale, et al: "HLA class II polymorphism contributes to specify desmoglein derived peptides in pemphigus vulgaris and pemphigus foliaceus", Journal of Autoimmunity, vol. 15, No. 1, p. 67-73 (Aug. 2000).

Meile W R, et al: "HLA pocket polymorphisms define functionally-active desmoglein 3 sequences in pemphigus vulgaris", Journal of Investigative Dermatology, vol. 121, No. 1, p. 0119, (Jul. 2003).

Moesta A. K., et al: "Identification of intracellular T cell epitopes in pemphigus vulgaris", Journal of Investigative Dermatology, vol. 119, No. 1, p. 319, Jul. 2002.

Wucherpfenning K.W., et al., "Structural Basis for Major Histocompatibility Complex (HMC)-Linked Subsceptibility to Autoimmunity: Charged Residues of a Single MHC Binding Pocket Confer Selective Presentation of Self-Peptides in Pemphigus Vulgaris", Proceedings of the National Academy of Sciences of USA, National Academy of Science. Washington, US. vol. 92, No. 25, 1995.

* cited by examiner

SEQUENCE LISTING

<160> NUMBER OF SEQ ID NOS: 3

<210> SEQ ID NO 1
<211> LENGTH: 19
<212> TYPE: PRT
<213> ORGANISM: Artificial Sequence
<220> FEATURE:
<223> OTHER INFORMATION: Polypeptide derived from human desmoglein 3
      protein

<400> SEQUENCE: 1

Glu Pro Asn His Leu Asn Ser Lys Ile Ala Phe Lys Ile Val Ser Gln
 1               5                  10                  15

Glu Pro Ala

<210> SEQ ID NO 2
<211> LENGTH: 6
<212> TYPE: PRT
<213> ORGANISM: Artificial Sequence
<220> FEATURE:
<223> OTHER INFORMATION: Sequence motif for Pemphigus vulgaris
      autoantigen

<400> SEQUENCE: 2

Leu Asn Ser Lys Ile Ala
 1               5

<210> SEQ ID NO 3
<211> LENGTH: 6
<212> TYPE: PRT
<213> ORGANISM: Artificial Sequence
<220> FEATURE:
<223> OTHER INFORMATION: Sequence motif for Pemphigus vulgaris
      autoantigen

<400> SEQUENCE: 3

Ile Ala Phe Lys Ile Val
 1               5

IDENTIFICATION OF SELF AND NON-SELF ANTIGENS IMPLICATED IN AUTOIMMUNE DISEASES

FIELD OF THE INVENTION

The present invention relates to the field of immunology and, in particular, to the identification of self and non-self antigens implicated in human autoimmune responses. The invention relates to methods of identifying such self antigens and provides examples of such antigens relating to pemphigus vulgaris. The invention also relates to the use of such antigens for in vitro assays, animal models, therapeutic agents and vaccines.

BACKGROUND OF THE INVENTION

Human autoimmune diseases have a striking genetic association with particular alleles of major histocompatability complex ("MHC") class I or class II genes. The field was established by the seminal discovery of HLA-B27 linked susceptibility to ankylosing spondylitis, a chronic inflammatory joint disease (Brewerton et al., 1973; Schlosstein et al., 1973). MHC associated susceptibility has now been documented for a variety of human autoimmune diseases, including insulin dependent diabetes mellitus (IDDM), rheumatoid arthritis (RA), pemphigus vulgaris (PV), multiple sclerosis (MS) and myasthenia gravis (MG), just to name a few (Todd et al., 1987; Ahmed et al., 1990; Ahmed et al. 1991; Lanchbury & Panayi, 1991; Spielman & Nathenson, 1982; Protti et al., 1993).

The MHC locus most commonly associated with autoimmune disease is the HLA-DRB locus (also known as DRB1), a highly polymorphic locus with over fifty known alleles. For example, a large body of epidemiological work has documented the association of rheumatoid arthritis with the DR4 (DRB1*0401, DRB1*0404) and DR1 (DRB1*0101) alleles, with the DR4 alleles conferring a higher risk than DR1 (Lanchbury & Panayi, 1991). The risk is dramatically increased when the subject is homozygous or heterozygous for DRB1*0401 and/or DRB1*0404. The observation that arthritis is associated with three DR alleles that are structurally similar led to the development of the 'shared epitope' hypothesis as DRB1*0401, 0404 and 0101 share critical polymorphic residues in the DRβ67–71 cluster (Gregersen et al. 1987; Lanchbury & Panayi, 1991). These residues (in particular DRβ71) appear to be critical in defining the selectivity of peptide binding to the disease associated molecules.

Pemphigus vulgaris (PV) is an autoimmune disease of the skin in which high titer auto-antibody production to an epidermal cell adhesion molecule (desmoglein 3) results in a loss of keratinocyte adhesion (acantholysis) and severe blister formation (Amagai et al., 1991). In different ethnic groups the disease is associated either with a DR4 allele (DRB1*0402) or with a rare DQ1 allele (DQB1*05032); only a small fraction of PV patients have neither susceptibility gene (Ahmed et al., 1991; Ahmed et al., 1990; Scharf et al., 1988). The DR4 subtype associated with pemphigus differs only at three positions in the DRβ67–71 cluster from the DR4 subtype associated with RA. The PV associated molecule has a negative charge (Glu) at the critical position (DRβ71); the neighboring position (DRβ70) is also negatively charged. The DR4 subtype associated with PV is the only one that carries a negative charge at DRβ71; a positive charge (Arg) is found at DRβ71 in the RA associated DR4 molecules.

Efforts to identify sequence homologies between self-peptide epitopes that might be involved in autoimmunity and various bacterial and viral pathogens have therefore been made. These homology searches have focused on alignments with sequence identity. No success has been reported using such alignments in identifying epitopes from pathogens that could cross react with presumably pathogenic T cell lines from human patients with autoimmune disease (Oldstone, 1990). A sequence identity was recently found between an epitope in a Coxsackie virus protein and GAD65, suspected of being an autoantigen in diabetes. These peptides could reciprocally generate polyclonal T cell lines from mice that cross react with the other peptides (Tian, et al., 1994). No evidence, however, was provided that these peptides could stimulate clones from diabetic mice (or humans).

Recent developments in the field, in particular the identification of allele specific peptide binding motifs have transformed the field (Madden et al., 1991; Rotschke & Falk, 1991). Based on this knowledge the structural basis for MHC linked susceptibility to autoimmune diseases can be reassessed at a level of detail sufficient for solving long-standing questions in the field. Motifs for peptide binding to several MHC class I and class II molecules have been defined by sequence analysis of naturally processed peptides and by mutational analysis of known epitopes. MHC class I bound peptides were found to be short (generally 8–10 amino acids long) and to possess two dominant MHC anchor residues; MHC class II bound peptides were found to be longer and more heterogeneous in size (Madden et al., 1991; Rotschke & Falk, 1991; Jardetzky et al. 1991, Chicz et al. 1993). Due to the size heterogeneity, however, it has proven more difficult to define MHC class II binding motifs based on sequence alignments. More recently, a crystal structure for HLA-DR1 demonstrated that there is a dominant hydrophobic anchor residue close to the N-terminus of the peptide and that secondary anchor residues are found at several other peptide positions (Brown et al., 1993). Even this work, however, could not provide a detailed description of the binding pockets of HLA-DR proteins, the particular residues involved in the formation of these pockets of the structural requirements or antigens for MHC binding.

In the present disclosure, a detailed description of the HLA-DR antigen binding pockets is provided (Stem et al., 1994). With this information, together with functional information defining those amino acids of the self or non-self antigen that are needed for MHC binding and TCR contact (e.g., Wucherpfennig et al. 1994a,), binding motifs for the various HLA-DR allotypes may be developed, self epitopes involved in autoimmune disease may be identified and a method is provided for identifying bacterial and viral epitopes which may initiate a human autoimmune response.

SUMMARY OF THE INVENTION

The present invention provides, in one aspect, isolated polypeptides derived from the human desmoglein 3 protein and implicated as self epitopes in the autoimmune disease pemphigus vulgaris (PV). These polypeptides consist essentially of the amino acid sequence disclosed herein and have been designated SEQ ID NO: 1. These polypeptides consist of SEQ ID NO: 1. In particular, the invention provides isolated polypeptides which consist of these sequences, the core MHC binding residues of these sequences, or the inner core MHC binding residues of these sequences.

Compositions of the present invention comprise a pharmaceutically acceptable carrier and a polypeptide of SEQ ID NO: 1. The composition can also comprise a pharmaceutically acceptable salt of the polypeptide. A preferred pharmaceutically acceptable salt is an acetate.

Compositions of the present invention can further comprising a pharmaceutically acceptable additive, such as a sugar or a surfactant. Acceptable sugars are those such as dextrose and mannitol. In one embodiment, the composition is formulated with about 5% sugar. The composition can further comprising buffers, such as dihydrate sodium citrate and monohydrate citric acid, and bulking agents, such as mannitol. In a further embodiment, a surfactant, such as can be polysorbate 20 or polysorbate 80, can be added to the composition in an amount of from about 0.01% to about 5%. One embodiment of the present invention comprises an immunogenic composition of the polypeptide.

In one embodiment, the composition comprises a lyophilized polypeptide of SEQ ID NO: 1. In one embodiment, the lyophilized polypeptide has a reconstitution time of less than 15 minutes, more preferably, the reconstitution time is less than 10 minutes, more preferably, the reconstitution time is less than 5 minutes, and more preferably, the reconstitution time is less than 3 minutes.

In one embodiment, the purity of the peptide is greater than 90%, more preferably, the purity is greater than 93%, more preferably, the purity is greater than 95%, and more preferably, the purity is greater than 96%.

In one embodiment, the composition has bacterial endotoxin contamination of less than about 5 EU/mL, more preferably, the bacterial endotoxin contamination is less than about 3 EU/mL, more preferably, the bacterial endotoxin contamination is less than about 2 EU/mL, and more preferably, the bacterial endotoxin contamination is less than about 1.25 EU/mL.

More preferably, the composition of the present invention has the formulation as set forth in Table 3.

In another set of embodiments, the invention provides for pharmaceutical preparations for use in tolerizing individuals to auto-antigens. The preparations include a pharmaceutically acceptable carrier and an isolated human polypeptide which includes an amino acid sequence corresponding to a sequence motif for an HLA-DR protein which is associated with a human autoimmune disease. These polypeptides are capable of binding to the HLA-DR protein to form a complex which activates autoreactive T cells in subjects having the autoimmune disease. The peptides are not derived from human collagen or human myelin basic protein.

In particular embodiments, such pharmaceutical preparations are provided in which the HLA-DR protein is HLA-DR4 protein and the autoimmune disease is pemphigus vulgaris. In addition, a particular sequence motif is provided for pemphigus vulgaris and pharmaceuticals having peptides with this motif are provided. Specific embodiments of the pharmaceuticals include each of the polypeptides described above with respect to pemphigus vulgaris. Thus, methods of tolerizing an individual to a pemphigus vulgaris autoantigen are also provided.

In another aspect of the invention, pharmaceuticals are provided for vaccination against a human pathogen implicated in the aetiology of autoimmune disease. These pharmaceutical preparations include a pharmaceutically acceptable carrier and an immunogenic preparation effective to immunize against a human pathogen. The human pathogen is one which in its native form includes a polypeptide having an amino acid sequence corresponding to a sequence motif for an HLA-DR protein which is associated with the autoimmune disease. These polypeptides are capable of binding to the HLA-DR protein to form a complex which activates T cells which become autoreactive and initiate the autoimmune disease. The preparations of the present invention specifically do not include such polypeptides but, rather, include other antigens from the pathogen.

In particular embodiments, such pharmaceutical preparations are provided in which the HLA-DR protein is HLA-DR4 protein and the autoimmune disease is pemphigus vulgaris. In addition, a particular sequence motif is provided for pemphigus vulgaris and pharmaceuticals which lack peptides having this motif are provided. Specific embodiments of the pharmaceuticals include preparations lacking each of the polypeptides described above with respect to pemphigus vulgaris. Thus, methods of immunizing an individual against pathogens which may cause pemphigus vulgaris are also provided.

The present invention also provides general methods for evaluating a peptide for an ability to induce an autoimmune response. These methods involve choosing an MHC HLA-DR molecule associated with the autoimmune response, selecting at least two major MHC binding pockets of the HLA-DR molecule, identifying sets of amino acid residues which bind within each of the selected pockets, developing a sequence motif for the HLA-DR molecule in which the sets of amino acids define the allowed amino acids at the corresponding positions of the motif, and then comparing the amino acid sequence of the peptide to the sequence motif. Peptides which match the motif have a much greater likelihood of inducing the autoimmune disease. In addition, if there is a known epitope implicated in the disease, the method may further include selecting at least one TCR contact residue of the epitope, identifying a set of amino acid residues which may serve as the TCR contact, and including this set in the motif at the appropriate position. In preferred embodiments, the motifs include restrictions on the residues at positions corresponding to at least the PI MHC binding pocket and at least one of the P4 and P6 pockets.

In another embodiment of the invention, methods are provided specifically for identifying foreign antigens implicated in human autoimmune response. These methods include the same steps as the previously described methods, but further include a comparison of the resulting sequence motif to sets of human pathogens. In preferred embodiments, peptide sequences from one or more species in the normal human intestinal flora are excluded from consideration. In another preferred embodiment, sequences from one or more species of pathogen which is negatively correlated with the incidence of the disease are excluded. In a most preferred embodiment, the human pathogen peptides are searched and evaluated on a computer database using the motif as a search criterion.

The present invention provides, in one aspect, isolated peptides derived from the human desmoglein 3 (Dsg3) protein, and uses thereof. These peptides, for example, consist essentially of SEQ ID NO: 1, and bind to a HLA-DR4 protein to form a complex which activates autoreactive T cells in a subject having pemphigus vulgaris.

Certain methods of the invention comprise administering to a subject a pharmaceutically effective amount of a Dsg3 peptide or peptidomimetic, which binds to a HLA-DR protein to form a complex which activates autoreactive T cells in subjects having the autoimmune disease. Administration of the peptidomimetic results in tolerization of the subject or can be used as a vaccine.

In further aspects, the invention provides nucleic acids comprising a coding sequence for a Dsg3 peptide that binds to a HLA-DR molecule. In certain embodiments, such nucleic acids may be used, for example, to produce Dsg3 peptides, including fusion proteins. In other embodiments, such nucleic acids may be administered to a subject so as to cause production of the Dsg3 peptide in vivo.

In certain aspects, the Dsg3 therapeutic comprises a fusion protein comprising a first polypeptide and a second polypeptide wherein the first polypeptide consists essentially of a Dsg3 peptide/peptidomimetic, and wherein the second polypeptide comprises a carrier protein, a production proteins, or a stabilizing protein.

In certain embodiments, the compounds of the present invention are represented by the following motifs:

```
E P N H L N S K I A F K I V S Q E P A  (SEQ ID NO:1)
      1     4   6                      Motif 1
            1     4   6                Motif 2
```

DETAILED DESCRIPTION OF THE INVENTION

I. Overview

A. The MHC Class II HLA-DR Molecular Mimicry Motif

The HLA-DR binding site is characterized by five major pockets which may bind the amino acid side chains of antigens (Stem et al., 1994, the entire disclosure of which is incorporated herein by reference). See FIG. 1. The amino acid residue of the antigen which binds in the first major pocket is designated P1. The remaining residues may then be numbered by their positions relative to P1 (with positive numbers increasing toward the carboxy terminus and negative numbers increasing toward the amino terminus):

P-i ... P-1 P1 P2 P3 P4 ... Pj.

Thus, the first major pocket of an HLA-DR molecule, by definition, binds the side chain of residue P1 on an antigen. The remaining major pockets bind residues P4, P6, P7 and P9. These residues are defined as the major MHC contact residues.

The amino acid side chains of residues P-1, P2, P3, P5, P8, and P11 are oriented away from the HLA-DR binding site and, therefore, are available as contact residues for a T cell receptor (TCR). All of these residues are defined as TCR contact residues.

B. The MHC Contact Residues

The first major pocket of the HLA-DR molecule is strongly hydrophobic. It is formed by a stretch of residues at about positions 85, 86, 89 and 90 of the β chain, a stretch of residues at about positions 31, 32 and 34 of the α chain, and side chains from residues at about positions 7 and 43 of the α chain. For example, in HLA-DR1 (DRA, DRB1*0101), the first pocket is formed by residues β85 (Val), β86 (Gly), β89 (Phe), β90 (Thr), α31 (Ile), α32 (Phe), α34 (Phe), α7 (Ile), and α43 (Trp). The corresponding residues for other HLA-DR alleles are known in the art (see, e.g., Marsh and Bodmer, 1992, incorporated by reference herein) and are available through genetic databases.

Although most of the residues that shape the P1 pocket are from the highly conserved DRα chain, the size and nature of this pocket varies due to polymorphisms in the β chain residues involved in the pocket. For the DRB1*0101 protein, the pocket is large and hydrophobic and can accommodate any of the aliphatic or aromatic residues. Polymorphism at the β residues, however, may alter the binding capacity of the P1 pocket. For example, the β86 residue is known to be polymorphic. Most commonly, this site is occupied by either Gly or Val. Generally, when Gly is present at β86 (as in DRB1*0101), any of the aliphatic or aromatic residues may bind within the pocket. When Val is present, however, the pocket is smaller and Tyr and Trp cannot be accommodated. Thus, when β86 is Gly, position P1 of the molecular mimicry motif may consist of residues chosen from V, L, I, A, M, F, Y, W and when β86 is Val, position P1 of the motif may consist of residues chosen from V, L, I, A, M, F. Similar considerations apply to the other β residues of the P1 pocket.

The P4 pocket of HLA-DR molecules is also a relatively large, shallow, hydrophobic pocket oriented across the antigen binding site. This pocket can bind a variety of large aliphatic side chains which can maintain hydrophobic interactions along the side and floor of the pocket. The pocket is formed by a stretch of residues at about positions 70, 71, 74 and 78 of the β chain, and side chains from residues at about position 13 of the β chain and about position 9 of the α chain. For example, in HLA-DR1 (DRA, DRB1*0101), the P4 pocket is formed by residues β70 (Gln), β71 (Arg), β74 (Ala), β78 (Tyr), β13 (Phe), and α9 (Gln). The corresponding residues for other HLA-DR alleles are known in the art (see, e.g., Marsh and Bodmer, 1992) and are available through genetic databases.

Like the P1 pocket, the P4 pocket is largely hydrophobic but its binding capacity is affected by polymorphisms at the β residues involved in the pocket. For example, different DR alleles have differently charged residues at position β71: In DRB1*0404, β71 is occupied by a positively charged Arg residue whereas in DRB1*0402 β71 is a negatively charged Glu residue. Thus, although this pocket can generally bind a variety of aliphatic or aromatic side chains (e.g., V, L, I, A, M, F, Y, W), positively charged P4 antigen residues are disfavored when β71 is positively charged and, similarly, negatively charged P4 residues are disfavored when β71 is also negative. Similar considerations apply to the other β residues of the P4 pocket. Note that some residues may be involved in forming each of two adjacent pockets (e.g., β13 in the P4 and P6 pockets) and therefore the occupancy of one of these pockets by a particular amino acid may influence the occupancy of the other.

The P6 pocket of HLA-DR molecules is a relatively shallow pocket with a preference for smaller (e.g., A, G) P6 antigen residues. The pocket is formed by the highly conserved α11, α62, α65 and α66 residues and the highly polymorphic β11 and β13 residues of the HLA-DR protein. For example, in HLA-DR1 (DRA, DRB1*0101), the P6 pocket is formed by residues α11 (Glu), α62 (Asn), α65 (Val), α66 (Asp), β11 (Leu) and β13 (Phe). The corresponding residues for other HLA-DR alleles are known in the art (see, e.g., Marsh and Bodmer, 1992) and are available through genetic databases.

Although there are only two β chain residues in the P6 pocket, they vary widely amongst the DR alleles. With a large Phe residue at β13 (as in DRB1*0101), the P6 residue is preferably one of the small residues (e.g., A, G). In other DR alleles, however, β13 is occupied by smaller or more polar residues such as the β13 (His) of DRB1*0401. For such alleles, the P6 motif may include somewhat larger and polar residues (e.g., S, T, V) but should still avoid the largest and aromatic residues. Finally, in some alleles, β11 and β13 are both serine residues (e.g., DRB1*1 101) and for these cases more hydrophilic or hydrogen bonding residues may be included in the motif.

The P7 pocket of HLA-DR molecules is also a relatively shallow pocket. The pocket is formed by five residues of the β chain: α8, β47, β61, β67 and β71. For example, in HLA-DR1 (DRA, DRB*0101), the P7 pocket is formed by residues β28 (Glu), β47 (Tyr), β61 (Trp), β67 (Leu) and β71 (Arg). The corresponding residues for other HLA-DR alleles are known in the art (see, e.g., Marsh and Bodmer, 1992) and are available through genetic databases. This pocket does not appear to contribute greatly to the specificity of HLA-DR1 but may be important in other alleles.

The P9 pocket of HLA-DR molecules is generally a small hydrophobic pocket and, therefore, small hydrophobic residues are preferred at the P9 position of the antigen. This pocket is formed by the conserved α chain residues α69, α72, α73 and α76 and by the polymorphic β chain residues β9 and β57. For example, in HLA-DR1 (DRA, DRB1*0101) the P9 pocket is formed by α69 (Asn), α72 (Ile), α73 (Met), α76 (Arg), β9 (Trp) and β57 (Asp). The corresponding residues for other HLA-DR alleles are known in the art (see, e.g., Marsh and Bodmer, 1992) and are available through genetic databases.

The P6, P7 and P9 pockets appear to be less important than the P1 and P4 pockets in binding to DR molecules but they may be more important in binding to other isotypes (e.g., the P9 pocket of DQ may be important).

C. The TCR Contact Residues

When there is no known or suspected antigen involved in an autoimmune response, the positions of the sequence motif corresponding to the TCR contact residues may be left unrestricted. That is, absent a known or suspected antigen, the TCR contact positions of the motif are preferably allowed to vary amongst all of the amino acids.

When, on the other hand, there is a known or suspected antigen involved in an autoimmune response, at least some of the motif positions corresponding to the TCR contact residues may be restricted according to the sequence of the antigen. Thus, for example, the P2 and/or P3 and/or P5 positions of the motif may be restricted to only those residues found at the corresponding positions of the antigen. Alternatively, at least some of the TCR contact residues of the motif may be restricted not just to the corresponding residues of the antigen but may be allowed to vary amongst similarly charged and/or structurally similar residues (e.g., K and R). It should be noted, however, that greater conservatism with respect to the TCR contact residues of the motif is justified by the presumably greater specificity of TCR binding relative to the known promiscuity of MHC binding.

D. Developing an HLA-DR Sequence Motif

Given the present disclosure of the HLA-DR residues involved in the formation of the P1, P4, P6, P7 and P9 MHC binding pockets, and given the nucleotide or corresponding amino acid sequence of any particular HLA-DR allele, one is now enabled to develop a sequence motif useful in evaluating or predicting the ability of peptides to bind to that MHC protein. When a particular antigen is known to (or is suspected of) binding to the MHC protein, the TCR contact residues of that antigen may also be considered in the motif.

The method first requires the selection of two or more of the MHC binding pockets for which the choice of peptide residues will be restricted at the corresponding positions of the motif. One may select all five of the major binding pockets and develop a motif in which the corresponding five positions of the motif are restricted or one may select fewer and develop a less restricted motif. As will be obvious to one of ordinary skill in the art, a more restricted motif will identify a lesser number of peptides in a database search and a less restricted motif will identify a greater number of peptides. In all instances, at least two of the major binding pockets should be selected. When fewer than all five MHC binding pockets are selected, it is preferred that at least one is P1 and that a second is chosen from P4, P6 and P9.

Either before or after the pockets to be restricted by the motif are selected, the set of amino acid side chains likely to bind within each of those pockets and, therefore, the set of amino acid residues that will define the corresponding positions of the motif, must be determined. This may be accomplished by one of ordinary skill in the art by considering the amino acid residues which form the pocket. These residues, identified in Section A above, will determine the size and nature (i.e., hydrophobic, hydrophilic, positively charged, negatively charged, uncharged) of the pocket and consequently, the side chains which may bind within the pocket. Reference may be made to FIG. 1 during these considerations but will become increasingly unnecessary as one develops familiarity with the variations of the pockets.

As a general matter, in light of the identification of the residues forming the MHC binding pockets of the HLA-DR proteins disclosed herein, one of ordinary skill in the art can easily develop a sequence binding motif for any HLA-DR protein for which these residues are known for two or more binding pockets. The major considerations are size, hydrophobicity and charge. In light of the present disclosure, each of these considerations may be addressed according to well-known principles. A baseline is disclosed herein for each pocket for the DRB1*0101 allele, and relative to this HLA-DR protein, one of ordinary skill is enabled to develop motifs for other HLA-DR alleles. Thus, substitutions which lead to larger/smaller pockets suggest that the corresponding motif positions should be restricted so as to permit smaller/larger residues. Similarly, more/less hydrophobic pockets suggest that the corresponding motif positions should be restricted to more/less hydrophobic residues. Finally, positively/negatively charged pockets suggest that positively/negatively charged residues should be excluded and negatively/positively charged residues may be included at the corresponding motif positions. As noted above, the present disclosure enables one of ordinary skill to develop motifs based upon these well-established principles.

For example, and not by means of limitation, consider the P1 pocket of the HLA-DR protein. The residues forming this pocket in the DRB1*0101 were described above. For DRB1*0101, the P1 pocket is large and hydrophobic and can accommodate any of the aliphatic or aromatic residues (e.g., V, L, I, A, M, F, Y, W). For the DRB1*1602 protein the same is true. On the other hand, in the DRB1*1501 protein, the β86 position is occupied by Val instead of the Gly found in DRB1*0101 and DRB1*1602. This substitution decreases the size of the P1 pocket in this MHC protein and, as a result, the pocket cannot easily accommodate Tyr or Trp side chains. Thus, for DRB1* 1501, the sequence motif at position P1 may be restricted to residues chosen from V, L, I, A, M and F.

Similarly, in light of the present disclosure, one of ordinary skill in the art may consider each of the MHC binding pockets, or only selected pockets, and develop a sequence motif for any HLA-DR protein for which the residues involved in pocket formation are known. These residues will determine both the size and nature of the pocket and, thereby, the size and nature of the residues which may bind within it. When the pocket is relatively small, the largest amino acid residues (e.g., Y, W) may be excluded from the corresponding position of the motif and alternatively, when the pocket is charged, amino acid residues of the same charge may be excluded.

If a self or foreign epitope involved in immune response is known or suspected, and particularly if its TCR contact residues can be defined through the use of responsive T cell clones, the TCR contact residues of the epitope may also be considered in developing a sequence motif. As with the MHC contact residues, all or merely some of the TCR contact residues may be restricted in the motif. And, as with the MHC positions, the restriction of more positions (or the greater restriction of any one position) will result in the identification of fewer peptides in a database search. Unlike the MHC contact residues, for which at least two positions should be restricted in the motif, it is acceptable to omit any restrictions of TCR contact residues in the motif.

If any TCR contact residue positions are restricted in the sequence motif, it is preferred that a position selected from positions P2, P3 and P5 be chosen. Because, in contrast to the relative promiscuity of MHC binding pockets, TCR contact residues appear to have greater specificity, it is preferred that any TCR contact residue positions which are restricted in the motif be rather narrowly restricted. That is, it is preferred that such positions be restricted to just the residue found at the corresponding position of the known antigen or just to residues which are highly similar in structure and charge.

Obviously, MHC and TCR positions not selected for restriction may be represented by, in the notation of this disclosure, an X. Similarly, as shown in the examples below, several motifs may be developed with varying numbers of positions restricted to varying extents.

II. Definitions

For clarity of interpretation and to clearly and distinctly point out the subject matter of the claimed invention, the following definitions are provided for several terms used in the claims appended hereto.

"Activate" or "activation" as used herein is intended to indicate that the subject Dsg3 peptide binds to a HLA-DR protein to form a complex which activates autoreactive T cells in subjects having an autoimmune disease.

By the terms "amino acid residue" and "peptide residue" is meant an amino acid or peptide molecule without the —OH of its carboxyl group. In general, the abbreviations used herein for designating the amino acids and the protective groups are based on recommendations of the IUPAC-IUB Commission on Biochemical Nomenclature (see *Biochemistry* (1972) 11: 1726–1732). For instance, Met, Ile, Leu, Ala and Gly represent "residues" of methionine, isoleucine, leucine, alanine and glycine, respectively. By the residue is meant a radical derived from the corresponding a-amino acid by eliminating the OH portion of the carboxyl group and the H-portion of the α-amino group. The term "amino acid side chain" is that part of an amino acid exclusive of the —CH—$(NH_2)COOH$ portion, as defined by K. D. Kopple, "Peptides and Amino Acids", W. A. Benjamin Inc., New York and Amsterdam, 1996, pages 2 and 33; examples of such side chains of the common amino acids are —$CH_2CH_2SCH_3$ (the side chain of methionine), —$CH_2(CH_3)$—$CH_2CH_3$ (the side chain of isoleucine), —$CH_2CH(CH_3)_2$ (the side chain of leucine) or H— (the side chain of glycine).

For the most part, the amino acids used in the application are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidoglycan bacterial cell walls.

The term amino acid residue further includes analogs, derivatives and congeners of any specific amino acid referred to herein, as well as C-terminal or N-terminal protected amino acid derivatives (e.g., modified with an N-terminal or C-terminal protecting group). For example, the present invention contemplates the use of amino acid analogs wherein a side chain is lengthened or shorted while still providing a carboxyl, amino or other reactive precursor functional group for cyclization, as well as amino acid analogs having variant side chains with appropriate functional groups).

An "amino acid motif" is a sequence of amino acids, optionally a generic set of conserved amino acids, associated with a particular functional activity.

The term "binding" refers to a direct association between two molecules, due to, for example, covalent, electrostatic, hydrophobic, ionic and/or hydrogen-bond interactions under physiological conditions, and including interactions such as salt bridges and water bridges.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A cell to be contacted with subject Dsg3 therapeutics includes a cell in culture, a cell that is part of an organized assemblage, such as an organ or tissue, or a cell that is part of an organism.

A "chimeric protein" or "fusion protein" is a fusion of a first amino acid sequence encoding a polypeptide with a second amino acid sequence defining a domain foreign to and not substantially homologous with any domain of the first amino acid sequence. A chimeric protein may present a foreign domain which is found (albeit in a different protein) in an organism which also expresses the first protein, or it may be an "interspecies", "intergenic", etc. fusion of protein structures expressed by different kinds of organisms.

The terms "compound", "test compound" and "molecule" are used herein interchangeably and are meant to include, but are not limited to, peptides, nucleic acids, carbohydrates, small organic molecules, natural product extract libraries, and any other molecules (including, but not limited to, chemicals, metals and organometallic compounds).

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include:

(i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp,
(v) a nitrogen ring group, consisting of His and Trp,
(vi) a large aliphatic nonpolar group, consisting of Val, Leu and Ile,
(vii) a slightly-polar group, consisting of Met and Cys,
(viii) a small-residue group, consisting of Ser, Thr, Asp, Asn, Gly, Ala, Glu, Gln and Pro,
(ix) an aliphatic group consisting of Val, Leu, Ile, Met and Cys, and
(x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art.

A "conserved residue" is an amino acid that is relatively invariant across a range of similar proteins. Often conserved residues will vary only by being replaced with a similar amino acid, as described above for "conservative amino acid substitution".

The term "consisting essentially of" as used in reference to a peptide including one or more designated amino acid sequences indicates that no more than 20 to 30 amino acids are added to the designated amino acid sequence(s), and furthermore that these additional amino acids do not substantially alter the function of the designated amino acid sequence(s). The term "consisting essentially of" as used in reference to a peptidomimetic indicates that no more than 20–30 amino acid mimetic units are added to the designated sequence, and that these added units do not substantially alter the function of the designated sequence.

An "effective amount" of, e.g., an Dsg3 peptide or peptidomimetic, with respect to the subject methods of treatment, refers to an amount of active ingredient in a preparation which, when applied as part of a desired dosage regimen brings about, e.g., binds to a HLA-DR4 protein to form a complex which activates autoreactive T cells in subjects having pemphigus vulgaris.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and BLAST) can be used (See www.ncbi.nlm.nih.gov).

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. *Applied Math.,* 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403–410 (1990) and Altschul et al. *Nuc. Acids Res.* 25: 3389–3402 (1997)). The BLAST X program is publicly available from NCBI and other sources (BLAST Manual, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

"Isolated" (used interchangeably with "substantially pure") when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature. By "isolated" it is further meant a protein that is: (i) synthesized chemically; or (ii) expressed in a host cell and purified away from associated and contaminating proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

A "patient" or "subject" to be treated by the subject method can mean either a human or non-human animal. The patient can be a mammal such as, a human, a primate (e.g., chimpanzee, gorilla, monkey), a domesticated animal (e.g., a dog, a horse, a cat, a pig, a cow), a rodent (e.g., a mouse or a rat), etc.

The terms "peptide", "polypeptide" and "protein" are used interchangeably herein. These terms refer to unmodified amino acid chains, and also include minor modifications, such as phosphorylations, glycosylations and lipid modifications. The terms "peptide" and "peptidomimetic" are not mutually exclusive and include substantial overlap. A "Dsg3 peptide" is a peptide consisting essentially of an amino acid motif of SEQ ID NO: 1.

A "peptidomimetic" includes any modified form of an amino acid chain, such as a phosphorylation, capping, fatty acid modification and including unnatural backbone and/or side chain structures. As described below, a peptidomimetic comprises the structural continuum between an amino acid chain and a non-peptide small molecule. Peptidomimetics generally retain a recognizable peptide-like polymer unit structure. A "Dsg3 peptidomimetic" is a peptidomimetic designed to mimic a Dsg3 peptide, retaining certain structural elements of the Dsg3 peptide, and retaining the function of binding to a HLA-DR4 protein forming a complex which activates autoreactive T cells in a patient having pemphigus vulgaris.

The phrase "protecting group" as used herein means substituents which protect the reactive functional group from undesirable chemical reactions. Examples of such protecting groups include esters of carboxylic acids and boronic acids, ethers of alcohols and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as to illustrate, formyl, dansyl, acetyl, benzoyl, trifluoroacetyl, succinyl and methoxysuccinyl; aromatic urethane protecting groups such as, for example, benzyloxycarbonyl (Cbz); and aliphatic urethane protecting groups such as t-butoxycarbonyl (Boc) or 9-Fluorenylmethoxycarbonyl (FMOC).

"Pharmaceutically acceptable carrier" is defined herein as a carrier that is physiologically acceptable to the administered patient and that retains the therapeutic properties of the peptides with which it is administered. Pharmaceutically-acceptable carriers and their formulations are well-known and generally described in, for example, *Remington's pharmaceutical Sciences* ($18^{th}$ Edition, ed. A. Gennaro, Mack Publishing Co., Easton, Pa., 1990). On exemplary pharmaceutically acceptable carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject peptides from the administration site of one organ, or portion of the body, to another organ, or portion of the body. Each carrier must be "acceptable" in the sense of being compatible with the other ingredients of the formulation and not injurious to the patient. Nor should a pharmaceutically acceptable carrier alter the specific activity of the subject peptides. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. "Small molecule" as used herein, is meant to refer to a composition, which has a molecular weight of less than about 5 kD and most preferably less than about 2.5 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures comprising arrays of small molecules, often fungal, bacterial, or algal extracts, which can be screened with any of the assays of the invention.

The letter "x" as used in amino acid sequences herein is intended to indicate that any of the twenty standard amino acids may be placed at this position. For the purposes of peptidomimetic design, an "x" in an amino acid sequence may be replaced by a mimic of the amino acid present in the target sequence, or the amino acid may be replaced by a spacer of essentially any form that does not interfere with the activity of the peptidomimetic.

In some aspects, the invention relates to Dsg3 therapeutics designed to act as mimics or decoys of a Dsg3 peptide comprising an amino acid motif of SEQ ID NO: 1. While not wishing to be bound to mechanism, it is expected that such peptides may binds to a HLA-DR protein to form a complex which activates autoreactive T cells in subjects having an autoimmune disease. Such therapeutics may, for example, comprise peptides, peptidomimetics, small molecules based on the amino acid sequence of Dsg3.

As used herein, "salts" include pharmaceutically-acceptable salts, esters, hydrates, solvates or other derivatives of the compounds include any such salts, esters and other derivatives that may be prepared by those of skill in this art using known methods for such derivatization and that produce compounds that may be administered to animals or humans without substantial toxic effects and that either are pharmaceutically active or are prodrugs. Pharmaceutically-acceptable salts include, but are not limited to, salts of alkali metals and alkaline earth metals, including but not limited to sodium salts, potassium salts, lithium salts, calcium salts and magnesium salts; transition metal salts, such as zinc salts, copper salts and aluminum salts; polycationic counter ion salts, such as but not limited ammonium and substituted ammonium salts and organic amine salts, such as hydroxyalkylamines and alkylamines; salts of mineral acids, such as but not limited to hydrochlorides and sulfates, salts of organic acids, such as but not limited acetates, lactates, malates, tartrates, citrates, ascorbates, succinates, butyrate, valerate and fumarates. Also contemplated herein are the corresponding esters.

The term "pharmaceutically acceptable salts" refers to the relatively non-toxic, inorganic and organic addition salts of the Dsg3 and MS peptides. These salts can be prepared in situ during the final isolation and purification of the peptides, or separating reacting a purified peptide in its free base form with a suitable organic or inorganic acid, and isolating the salt thus formed. Representative salts include the hydrochloride, hydrobromic, sulfate, bisulfate, phosphate, nitrate, acetate, valerate, oleate, palmitate, stearate, laurate, benzoate, lactate, tosylate, citrate, maleate, fumarate, succinate, tartrate, napthylate, mesylate, glucoheptonate, lactobionate, and laurlysulphonate salts and the like. (See, for example, Berge et al. (1977) "Pharmaceutical Salts", *J. Pharm. Sci.* 66: 1–19)

The term "sequence motif," in accordance with the description provided herein, means a series of restrictions on the residues which may occupy certain relative positions of an amino acid sequence. A sequence motif must restrict at least three and preferably four or five positions of an amino acid sequence. The relative positions of the first (N-terminal) and last (C-terminal) restricted amino acid positions shall be separated by at least two but no more than twelve amino acid residues. For example, P1 and P4 may be the first and last restricted residues and these residues are separated by two residues. As another example, P1 and P11 may be the first and last restricted residues and these are separated by ten residues.

Positions between the first and last restricted positions may be restricted or unrestricted with the exception that a total of at least three positions of the motif must be restricted. Of the three positions which must be restricted, at least two must be residues corresponding to major MHC binding pockets. If only two of the restricted residues correspond to MHC binding residues, the third must correspond to a TCR contact residue. Further, at least one of the positions restricted must correspond to either the P1 or P4 binding position. By "restricted" is meant that at least one, and preferably ten, amino acid residues shall be excluded from a position.

An amino acid sequence "corresponds" to a sequence motif if it can be aligned with the positions of the sequence motif such that at each restricted position of the motif the amino acid sequence includes a residue which is not excluded from that position by the restrictions which define the motif. As the restrictions which define the motif are derived from the size and nature of the MHC binding pockets of HLA-DR proteins and optionally, the TCR contact residues of known epitopes, the restricted positions of the binding motif may also be said to correspond to the MHC binding pockets and TCR contact residues.

The term "isolated," in reference to a protein or polypeptide, means separated from its native or natural chemical microenvironment. Thus, a polypeptide isolated from a bacterium shall be in a preparation substantially free of most of the other bacterial polypeptides; and similarly, an isolated viral polypeptide preparation shall be substantially free of the other polypeptides which comprise the virus.

The term "associated with" as used in connection with a particular HLA-DR protein and an autoimmune disease or autoimmune response, shall mean that the protein and the disease/response have been positively correlated by clinical or epidemiological studies such that the likelihood of developing the disease/response has been shown to be increased by presence of the protein.

The term "HLA-DR protein" refers to a particular protein product of a particular allele of the MHC class II HLA-DR gene. A disease associated with an HLA-DR protein is one associated with such a particular protein and not merely with the HLA-DR gene locus.

The term "human pathogen" refers to a bacterium, virus or protozoan capable of infecting humans and generating an immune response. The term "specifically" is intended to exclude the bacteria which form part of the normal human intestinal flora. By this term, "normal human intestinal flora" is meant the bacteria which normally inhabit the human gut, such as *Escherichia coli*, but which do not normally cause disease.

The term "autoreactive" as applied to T cells refers to T cells from a human which are activated by a human self epitope. By "activation" of T cells is meant induction to proliferate, secrete lymphokines (cytokines) and/or to initiate effector activity (e.g. cytotoxicity).

The term "autoantigen" is meant a self protein or polypeptide which includes a "self epitope." By "self epitope" is meant that part of an autoantigen which is recognized by T cells when bound to and presented by a MHC molecule.

The term "effective amount" with respect to tolerizing an individual to an antigen is an amount of the antigen sufficient to render T cells otherwise specific for the antigen unresponsive to the antigen when bound to, and presented by, an MHC molecule. T cells which are unresponsive fail to activate when presented with the antigen for which they are specific. The term "effective amount" with respect to immunizing an individual to an antigen is an amount sufficient to induce an immune response which results in T cells specific for the antigen. Typical ranges of dosages are from 1 nanogram/kilogram to 100 milligrams/kilogram or even 500 milligrams/kilogram. Effective amounts will vary according to such factors as age, sex and sensitivity to the antigen.

The term "core MHC binding residues" refers to the residues of an epitope corresponding to the P1 to P9 positions of a peptide bound to an HLA-DR molecule. The term "inner core MHC binding residues" refers to those residues of an epitope corresponding to the P1 to P6 positions of a peptide bound to an HLA-DR molecule.

III. Embodiments of the Invention

A. Peptides/Compositions/Peptidomimetics

The present invention provides for human desmoglein 3 (Dsg3) peptides and peptidomimetics. Dsg3 peptides include hose peptides that comprise a structural motif of SEQ ID NO: 1 with either motif #1 or motif #2. Optionally, the peptide will act to bind to a HLA-DR protein to form a complex which activates autoreactive T cells in subjects having an autoimmune disease. More specifically, the peptide of SEQ ID NO: 1 binds to a HLA-DR4 protein, thereby forming a complex which activates autoreactive T cells in a subject/patient having pemphigus vulgaris.

In one embodiment, the polypeptide consists essentially of an amino acid sequence represented by SEQ ID NO: 1. Alternatively, the polypeptide consists of SEQ ID NO: 1.

In a further invention, the compositions of the present invention further comprise a pharmaceutically acceptable additive in order to improve the stability of the peptide in composition and/or to control the release rate of the composition. Pharmaceutically acceptable additives of the present invention do not alter the specific activity of the subject peptide. A preferable pharmaceutically acceptable additive is a sugar such as mannitol, sorbitol, glucose, xylitol, trehalose, sorbose, sucrose, galactose, dextran, dextrose, fructose, lactose and mixtures thereof. Preferably, the sugar of the present invention is dextrose. Pharmaceutically acceptable additives of the present invention can be combined with pharmaceutically acceptable carriers and/or excipients such as dextrose. More preferably, the compositions of the present invention are formulated for administration with 5% dextrose. Alternatively, a preferable pharmaceutically acceptable additive is a surfactant such as polysorbate 20 or polysorbate 80 to increase stability of the peptide and decrease gelling of the pharmaceutical solution.

More preferably, the surfactant is added to the composition in an amount of 0.01% to 5% of the solution. Addition of such pharmaceutically acceptable additives increases the stability and half-life of the composition in storage.

In certain embodiments, a subject Dsg3 therapeutic comprises a peptidomimetic of a Dsg3 peptide (a Dsg3 peptidomimetic). Peptidomimetics are compounds based on, or derived from, peptides and proteins. The Dsg3 peptidomimetics of the present invention typically can be obtained by structural modification of a known Dsg3 peptide sequence using one or more unnatural amino acids, conformational restraints, isosteric replacements, and the like. The subject peptidomimetics constitute the continuum of structural space between peptides and non-peptide synthetic structures; Dsg3 peptidomimetics may be useful, therefore, in delineating pharmacophores and in helping to translate peptides into non-peptide compounds with the activity of the parent Dsg3 peptides.

Dsg3 peptidomimetics can have such attributes as being non-hydrolyzable (e.g., increased stability against proteases or other physiological conditions which degrade the corresponding peptide) or increased specificity and/or potency for binding to a HLA-DR protein to form a complex which activates autoreactive T cells in subjects having an autoimmune disease. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) *Tetrahedron Letters* 26:647; and Sato et al. (1986) *J. Chem. Soc. Perkin. Trans.* 1:1231), b-aminoalcohols (Gordon et al. (1985) *Biochem. Biophys. Res. Commun.* 126:419; and Dann et al. (1986) *Biochem. Biophys. Res. Commun.* 134:71), diaminoketones (Natarajan et al. (1984) *Biochem. Biophys. Res. Commun.* 124:141), methyleneamino-modifed (Roark et al. in Peptides: Chemistry and Biology, G. R. Marshall ed., ESCOM Publisher: Leiden, Netherlands, 1988, p 134), vinylogous polypeptides (Hagihara et al. (1992) *J. Am. Chem. Soc.* 114: 6568–70), oligoanthranilamides (Hamuro et al. (1996) *J. Am. Chem. Soc.* 118: 7529–41), vinylogous sulfonaminopeptides (Genarri et al. (1996) *Chem. Eur. J.* 2: 644–55), aedemers (Lokey et al. (1995) *Nature* 375: 303–5), and sugar-based peptidomimetics (Horvat et al. (1998) *J. Chem. Soc. Perkins Trans.* 1: 1789–95). Also, see generally, Session III: Analytic and synthetic methods, in Peptides: Chemistry and Biology, G. R. Marshall ed., ESCOM Publisher: Leiden, Netherlands, 1988). In addition, U.S. Pat. No. 5,422,426 describes high throughput and combinatorial methods for producing peptides and peptidomimetics.

In further embodiments, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Additionally, peptidomimetics based on more substantial modifications of the backbone of the Dsg3 peptide can be used. Peptidomimetics which fall in this category include (i) retro-inverso analogs, and (ii) N-alkyl glycine analogs (so-called peptoids, see e.g. Simon et al. (1992) *Proc. Natl. Acad. Sci. USA* 89: 9367–71) and others mentioned above.

Such retro-inverso analogs can be made according to the methods known in the art, such as that described by the Sisto et al. U.S. Pat. No. 4,522,752. For example, a retro-inverso analog can be generated as follows. The first step is to form a geminal diamine analog of an amino acid. The geminal diamine corresponding to the N-terminal amino acid, for example an N-terminal proline is synthesized by treating an N-protected proline analog with ammonia under HOBT-DCC coupling conditions to yield an unsubstituted amide, and then effecting a Hofmann-type rearrangement with I,I-bis-(trifluoroacetoxy)iodobenzene (TIB), as described in Radhakrishna et al. (1979) *J. Org. Chem.* 44:1746, effectively removing the carbonyl moiety from the unsubstituted amide. The product amine is then coupled to a side-chain protected (e.g., as the benzyl ester) second amino acid, such as N-Fmoc D-Thr residue under standard conditions to yield the pseudodipeptide. The Fmoc (fluorenylmethoxycarbonyl) group is removed with piperidine in dimethylformamide, and the resulting amine is trimethylsilylated with bistrimethylsilylacetamide (BSA) before condensation with suitably alkylated, side-chain protected derivative of Meldrum's acid as described in U.S. Pat. No. 5,061,811 (Pinori et al.) to yield a retro-inverso tripeptide. Meldrum's acid is a cyclic malonate analog where the R substitution on the fifth carbon (the carbon between the carbonyl groups) determines the amino acid moiety added. For instance, if the R group in Meldrum's acid is a methyl group, then an alanine moiety is added and the retro-inverso tripeptide has the formula PTA. The remaining ester group from the ring opening reaction with Meldrum's acid is further coupled with an amino acid analog under standard conditions to give the protected tetrapeptide analog. The protecting groups are removed to release the product and the steps repeated to elongate the tetrapeptide to the full length peptidomimetic. It will be generally understood that a mixed peptide, e.g. including some normal peptide linkages, will be generated by this process. As a general guide, sites which are most susceptible to proteolysis are typically altered, with less susceptible amide linkages being optional for mimetic switching. The final product, or intermediates thereof, can be purified by HPLC. Another embodiment involves building the retro-inverso tetrapeptide from the C-terminus using similar protective chemistry techniques.

Retro-enantio analogs such as this can be synthesized commercially available D-amino acids (or analogs thereof) and standard solid- or solution-phase peptide-synthesis techniques. For example, in a preferred solid-phase synthesis method, a suitably amino-protected (t-butyloxycarbonyl, Boc) residue (e.g. D-proline) is covalently bound to a solid support such as chloromethyl resin. The resin is washed with dichloromethane (DCM), and the BOC protecting group removed by treatment with TFA in DCM. The resin is washed and neutralized, and the next Boc-protected D-amino acid (e.g. D-Thr) is introduced by coupling with diisopropylcarbodiimide. The resin is again washed, and the cycle repeated for each of the remaining amino acids in turn (D-Ala, D-Pro, etc). When synthesis of the protected retro-enantio peptide is complete, the protecting groups are removed and the peptide cleaved from the solid support by treatment with hydrofluoric acid/anisole/dimethyl sulfide/ thioanisole. The final product is purified by HPLC to yield the pure retro-enantio analog.

The trans olefin analog of a Dsg3 peptide can be synthesized according to the method of Y.K. Shue et al. (1987) Tetrahedron Letters 28:3225. Other pseudo-dipeptides can be made by the method set forth above merely by substitution of the appropriate starting Boc amino acid and Wittig reagent. Variations in the procedure may be necessary according to the nature of the reagents used, but any such variations will be purely routine and will be apparent to one of skill in the art.

It is further possible couple the pseudo-dipeptides synthesized by the above method to other pseudo-dipeptides, to make peptide analogs with several olefinic functionalities in place of amide functionalities. For example, pseudo-dipeptides corresponding to Pro-Pro or Glu-Tyr, etc. could be made and then coupled together by standard techniques to yield an analog of the Dsg3 peptide which has alternating olefinic bonds between residues.

The synthesis of phosphonate derivatives can be adapted from known synthesis schemes. See, for example, Loots et al. in Peptides: Chemistry and Biology, (Escom Science Publishers, Leiden, 1988, p. 118); Petrillo et al. in Peptides: Structure and Function (Proceedings of the 9th American Peptide Symposium, Pierce Chemical Co. Rockland, Ill., 1985).

Many other peptidomimetic structures are known in the art and can be readily adapted for use in the subject Dsg3 peptidomimetics. To illustrate, the Dsg3 peptidomimetic may incorporate the 1-azabicyclo[4.3.0]nonane surrogate (see Kim et al. (1997) *J. Org. Chem.* 62:2847), or an N-acyl piperazic acid (see Xi et al. (1998) *J. Am. Chem. Soc.* 120:80), or a 2-substituted piperazine moiety as a constrained amino acid analogue (see Williams et al. (1996) *J. Med. Chem.* 39:1345–1348). In still other embodiments, certain amino acid residues can be replaced with aryl and bi-aryl moieties, e.g., monocyclic or bicyclic aromatic or heteroaromatic nucleus, or a biaromatic, aromatic-heteroaromatic, or biheteroaromatic nucleus.

In certain embodiments, the subject Dsg3 peptide or peptidomimetic is capped at either the N-terminus (or other end structure at the normal N-terminus such as a carbonyl), the C-terminus (or other end structure at the normal C-terminus, such as an amine), or both. For example, a Dsg3 therapeutic may comprise a polypeptide comprising one or more Dsg3 sequences where the polypeptide has either an acetyl cap at the N-terminus, an amide cap at the C-terminus, or both. Methods for synthesizing capped peptides are disclosed, for example, in U.S. Pat. No. 5,994,309.

The subject Dsg3 peptidomimetics can be optimized by, e.g., combinatorial synthesis techniques combined with such high throughput screening as described herein.

Moreover, other examples of peptidomimetics include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A peptidomimetic can be obtained by, for example, screening libraries of natural and synthetic compounds for compounds capable of binds to a HLA-DR protein to form a complex which activates autoreactive T cells in subjects having, for example, pemphigus vulgaris. A peptidomimetic can also be obtained, for example, from libraries of natural and synthetic compounds, in particular, chemical or combinatorial libraries (i.e., libraries of compounds that differ in sequence or size but that have the same building blocks).

In certain aspects, subject Dsg3 therapeutic molecules, such as peptidomimetics and small molecules, may be obtained by rational design. In an exemplary rational design procedure, the three-dimensional structure of a target peptide of the present invention can be analyzed by, for example, nuclear magnetic resonance (NMR) or x-ray crystallography. The three-dimensional structure can then be used to predict structures of potential Dsg3 therapeutics by, for example, computer modeling. The predicted Dsg3 therapeutic structures can then be produced by, for example, chemical synthesis, recombinant DNA technology, or by isolating a molecule from a natural source (e.g., plants, animals, bacteria and fungi). Accordingly, a Dsg3 therapeutic may be modeled on an unconstrained polypeptide chain of one of the above-mentioned sequences. Where the target peptide is unconstrained, the desired structure may be modeled without resort to NMR or X-ray crystallography, and any of a number of programs for modeling short peptide chains may be employed.

In certain embodiments, Dsg3 peptides, peptidomimetics and small molecules are able to binds to a HLA-DR protein to form a complex which activates autoreactive T cells in subjects having an autoimmune disease. In an exemplary embodiment, a Dsg3 peptide, peptidomimetic or small molecule comprising a portion based on SEQ ID NO: 1 will binds to a HLA-DR4 protein to form a complex which activates autoreactive T cells in subjects having pemphigus vulgaris. Optionally, peptides, peptidomimetics and small molecules have a $K_D$ that is no more than ten times greater than the $K_D$ of the Dsg3 peptide on which they are based, and optionally have a roughly equivalent $K_D$ or a $K_D$ ten times lower or less.

In a further invention, the compositions of the present invention further comprise a pharmaceutically acceptable additive in order to improve the stability of the peptide in composition and/or to control the release rate of the composition. Pharmaceutically acceptable additives of the present invention do not alter the specific activity of the subject peptide. A preferable pharmaceutically acceptable additive is a sugar such as mannitol, sorbitol, glucose, xylitol, trehalose, sorbose, sucrose, galactose, dextran, dextrose, fructose, lactose and mixtures thereof. Preferably, the sugar of the present invention is dextrose. Pharmaceutically acceptable additives of the present invention can be combined with pharmaceutically acceptable carriers and/or excipients such as saline.

B. Fusion Proteins

Dsg3 peptides and peptidomimetics may be incorporated into fusion proteins. In general, the fusion protein provides a second functional portion, such as, for example, a carrier protein, a production protein or a stabilizing protein.

Useful carrier proteins include, for example, bacterial hemolysins or "blending agents", such as alamethicin or sulfhydryl activated lysins. Other carrier moieties which may be used include cell entry components of bacterial toxins, such as Pseudomonas exotoxin, tetanus toxin, ricin toxin, and diphtheria toxin. Also useful is melittin, from bee venom.

Stability proteins include proteins that increase the stability of the Dsg3 peptide, peptidomimetic or antibody. Production proteins include proteins that assist in production of the Dsg3 peptide. It is widely appreciated that fusion proteins can facilitate the expression of proteins, and accordingly, can be used in the expression of the Dsg3 peptides of the present invention. Exemplary production peptides include GST, polyhistidine, cellulose binding protein, chitin binding protein, etc. For example, Dsg3 peptides can be generated as glutathione-S-transferase (GST-fusion) proteins. Such GST-fusion proteins can enable easy purification of Dsg3 peptides, as for example by the use of glutathione-derivatized matrices (see, for example, Current Protocols in Molecular Biology, eds. Ausubel et al. (N.Y.: John Wiley & Sons, 1991)). In another embodiment, a fusion gene coding for a purification leader sequence, such as a poly-(His)/enterokinase cleavage site sequence, can be placed at the N-terminus of the Dsg3 peptide in order to permit purification of the poly(His)-Dsg3 peptide protein by affinity chromatography using a $Ni^{2+}$ metal resin. The purification leader sequence can, if desired, be subsequently removed by treatment with enterokinase (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

Nucleic acids encoding fusion proteins may be operatively linked to regulatory sequences and introduced into appropriate expression systems using conventional recombinant DNA procedures.

C. Introduction of Nucleic Acids

In another aspect, the present invention relates to constructs containing a nucleic acid encoding, for example in an exemplary method, a Dsg3 peptide of the present invention operably linked to at least one transcriptional regulatory sequence for introduction into and expression in a virus-infected cell. The gene constructs of the present invention are formulated to be used as a part of, for example, a gene therapy protocol to deliver the subject therapeutic protein to an animal to be treated.

Any of the methods known to the art for the insertion of DNA fragments into a vector may be used to construct expression vectors consisting of appropriate transcriptional/translational control signals and the desired nucleic acid sequence, such as an Dsg3 peptide-encoding nucleotide sequence or a nucleic acid encoding a peptide that binds to a HLA-DR protein to form a complex which activates autoreactive T cells in subjects having an autoimmune disease. (See, for example, Maniatis T., Fritsch E. F., and Sambrook J. (1989): Molecular Cloning (A Laboratory Manual), Cold Spring Harbor Laboratory, Cold Spring Harbor, N.Y.; and Ausubel F. M., Brent R., Kingston R. E., Moore, D. D., Seidman J. G., Smith J. A., and Struhl K. (1992): Current Protocols in Molecular Biology, John Wiley & Sons, New York). These methods may include in vitro DNA recombinant and synthetic techniques and in vivo genetic recombination. Expression of a subject nucleic acid may be regulated by a second nucleic acid sequence so that the encoded polypeptide is expressed in a host infected or transfected with the recombinant DNA molecule. For example, expression of a Dsg3 peptide may be controlled by any promoter/enhancer element known in the art. The promoter activation may be tissue specific or inducible by a metabolic product or administered substance.

Promoters/enhancers which may be used to control the expression of the Dsg3 peptide in vivo include, but are not limited to a promoter used by the target virus, the cytomegalovirus (CMV) promoter/enhancer (Karasuyama et al., 1989, *J. Exp. Med.,* 169:13), the human b-actin promoter (Gunning et al. (1987) *PNAS* 84:4831–4835), the glucocorticoid-inducible promoter present in the mouse mammary tumor virus long terminal repeat (MMTV LTR) (Klessig et al. (1984) *Mol. Cell Biol.* 4:1354–1362), the long terminal repeat sequences of Moloney murine leukemia virus (MuLV LTR) (Weiss et al. (1985) RNA Tumor Viruses, Cold Spring Harbor Laboratory, Cold Spring Harbor, N.Y.), the SV40 early or late region promoter (Bernoist et al. (1981) *Nature* 290:304–310; Templeton et al. (1984) *Mol. Cell Biol.,* 4:817; and Sprague et al. (1983) *J. Virol.,* 45:773), the promoter contained in the 3' long terminal repeat of Rous sarcoma virus (RSV) (Yamamoto et al., 1980, *Cell,* 22:787–797), the herpes simplex virus (HSV) thymidine kinase promoter/enhancer (Wagner et al. (1981) *PNAS* 82:3567–71), and the herpes simplex virus LAT promoter (Wolfe et al. (1992) *Nature Genetics,* 1:379–384), and Keratin gene promoters, such as Keratin 14.

Expression constructs of the subject Dsg3 therapeutic polypeptides may be administered in any biologically effective carrier, e.g. any formulation or composition capable of effectively delivering the recombinant gene to cells in vivo. Approaches include insertion of the Dsg3 peptide coding sequence in viral vectors including recombinant retroviruses, adenovirus, adeno-associated virus, and herpes simplex virus-1, or recombinant eukaryotic plasmids. Viral vectors transfect cells directly; plasmid DNA can be delivered with the help of, for example, cationic liposomes (lipofectin) or derivatized (e.g. antibody conjugated), polylysine conjugates, gramicidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid into a cell is by use of a viral vector containing nucleic acid encoding the particular Dsg3 peptide desired. Infection of cells with a viral vector has the advantage that a large proportion of the targeted cells can receive the nucleic acid. Additionally, molecules encoded within the viral vector, e.g., the recombinant Dsg3 peptide, are expressed efficiently in cells which have taken up viral vector nucleic acid.

In addition to viral transfer methods, such as those illustrated above, non-viral methods can also be employed to cause expression of a Dsg3 peptide in the tissue of an animal. Most non-viral methods of gene transfer rely on normal mechanisms used by mammalian cells for the uptake and intracellular transport of macromolecules. In preferred embodiments, non-viral gene delivery systems of the present invention rely on endocytic pathways for the uptake of the Dsg3 peptide-encoding gene by the targeted cell. Exemplary gene delivery systems of this type include liposomal derived systems, poly-lysine conjugates, and artificial viral envelopes.

In clinical settings, the gene delivery systems for the therapeutic Dsg3 peptide coding sequence can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or "gene gun" techniques. In preferred embodiments, the gene therapy construct of the present invention is applied topically to an infected or transformed cells of the skin or mucosal tissue. A Dsg3 peptide gene construct can, in one embodiment, be delivered in a gene therapy construct by electroporation using techniques described, for example, by Dev et al. ((1994) *Cancer Treat. Rev.* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

D. Salts

Of interest are formulations of pharmaceutically acceptable derivatives, including salts, esters, acids and bases, solvates, hydrates and prodrugs of the sulfonamides. In particular, derivatives of neutral sulfonamide compounds that yield formulations of greater stability than formulations containing the corresponding neutral compounds are provided. Preferred are salts, particularly alkali metal salts, and more preferably sodium salts, including salts prepared from sodium compounds, including, but not limited to, sodium bicarbonate in which the resulting product is a sodium salt and disodium hydrogen phosphate in which the resulting compound is a sodium hydrogen phosphate salt. The sodium salt of each compound is most preferred.

The sulfonamides from which the derivatives, particularly the salts, preferably sodium salts, are prepared have formula I:

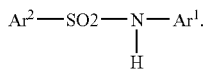

The salt derivatives include, but are not limited to, salts of alkali metals and alkaline earth metals, including but not limited to sodium salts, potassium salts, lithium salts, calcium salts and magnesium salts; transition metal salts, such as zinc salts, copper salts, gold salts and silver salts, and other metal salts, such as aluminum salts; cationic and polycationic counter ion salts, such as but not limited to ammonium and substituted ammonium salts and organic amine salts, such as hydroxyalkylamines and alkylamines; salts of mineral acids, such as but not limited to hydrochlorides and sulfates; salts of organic acids, such as but not limited to acetates, lactates, malates, tartrates, citrates, ascorbates, succinates, butyrates, valerates and fumarates. Also contemplated herein are the corresponding esters of any of the acids.

Among the preferred salts are: the salts of acetates, including trifluoroacetate, N,'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkyl amines, piperazine, tris (hydroxymethyl)aminomethane, aluminum, calcium, lithium, magnesium, potassium, sodium hydrogen phosphate, disodium phosphate, sodium, zinc, barium, gold, silver and bismuth. Alkali metals, particularly sodium salts, are preferred herein.

The formulations are compositions suitable for administration by any desired route and include solutions, suspensions, emulsions, tablets, dispersible tablets, pills, capsules, powders, dry powders for inhalers, sustained release formulations, aerosols for nasal and respiratory delivery, patches for transdermal delivery and any other suitable route. The compositions should be suitable for oral administration, parenteral administration by injection, including subcutaneously, intramuscularly or intravenously as an injectable aqueous or oily solution or emulsion, transdermal administration and other selected routes.

Lyophilized powders of the sulfonamide derivatives, methods for preparation thereof, and formulations containing reconstituted forms of the lyophilized powders are also provided. Vials and ampules and syringes and other suitable vessels containing the powders are also provided.

Such sulfonamides are those described in U.S. Pat. Nos. 5,464,853, 5,594,021, 5,591,761, 5,571,821, 5,514,691, 5,464,853, 5,962,490; and published International PCT application Nos. WO 96/31492 and WO 97/27979, each of which is hereby incorporated by reference in its entirety.

The formulations provided herein are for administration by a selected route and contain effective concentrations of pharmaceutically-acceptable salts of the above-noted compounds. The formulations deliver amounts effective for the treatment of autoimmune diseases, such as pemphigus vulgaris, are also provided.

Capsules and tablets containing the sodium salt of a sulfonamide are also preferred. Particularly preferred formulations are those that deliver amounts effective for the treatment of pemphigus vulgaris. The effective amounts and concentrations are effective for ameliorating any of the symptoms of any of the disorders.

In other embodiments, the formulations are solid dosage forms or gels, preferably capsules or tablets. In a preferred embodiment, the formulations are capsules containing an effective amount, typically about 10–100%, preferably about 50 to 95%, more preferably about 75–85%, most preferably about 80–85%, by weight, of one or more sodium hydrogen phosphate or sodium, preferably sodium, salts of one or more sulfonamide compounds of formula I; about 0 to 25%, preferably 8–15%, of an diluent or a binder, such as lactose or microcrystalline cellulose; about 0 to 10%, preferably about 3–7%, of a disintegrant, such as a modified starch or cellulose polymer, particularly a cross-linked sodium carboxymethyl cellulose, such as crosscarmellose sodium (Crosscarmellose sodium NF is available commercially under the name AC-DI-SOL, FMC Corporation, Philadelphia, Pa.) or sodium starch glycolate; and 0–2%, preferably 0.1–2%, of a lubricant, such a magnesium stearate, talc and calcium stearate. The disintegrant, such as crosscarmellose sodium or sodium starch glycolate, provides for rapid break-up of the cellulosic matrix for immediate release of active agent following dissolution of coating polymer. In all embodiments, the precise amount of active ingredient and auxiliary ingredients can be determined empirically and is a function of the route of administration, the disorder, and the age, sex, and health of the patient being treated.

In an exemplary embodiment, the formulations are capsules containing about 80–90%, preferably about 83% of one or more sodium salts of one or more sulfonamide compounds of formula I; about 10–15%, preferably about 11% of an diluent or a binder, such as lactose or microcrystalline cellulose; about 1–10%, preferably about 5% of a disintegrant, such as crosscarmellose sodium or sodium starch glycolate; and about 0.1 to 5%, preferably about 1% of a lubricant, such as magnesium stearate.

In another embodiment described in detail herein, the formulations are capsules containing 80–90%, preferably about 80–85%, depending upon the selected compound and indication, of one or more sodium salts of one or more sulfonamide compounds of formula I; about 10–15%, preferably 11% of microcrystalline cellulose; about 1–10%, preferably about 5% of a disintegrant, such as crosscarmellose sodium or sodium starch glycolate; and about 0.1 to 5%, preferably 1% of magnesium stearate. Solid forms for administration as tablets are also contemplated herein.

Preferred formulations are prepared from a sterile lyophilized powder containing a sodium salt of a sulfonamide. The lyophilized powders and methods of preparing the powders are also provided herein. In one embodiment, the compositions are provided in the form of lyophilized solids containing one or more sodium hydrogen phosphate or sodium, preferably sodium, salts of one or more sulfonamide compounds of formula I, and also contain one or more of the following:

(a) a buffer, such as sodium or potassium phosphate, or citrate;

(b) a solubilizing agent, such as LABRASOL (polyethylene glycol-8 caprylic capric glycerides sold by Gattefosse SA, France), dimethylsulfoxide (DMSO), bis(trimethylsilyl) acetamide, ethanol, propyleneglycol (PG), or polyvinylpyrrolidine (DSG3P); and (c) a sugar or other such carbohydrate, such as sorbitol or dextrose (typically in the range of about 1%–20%, preferably about 5%–15%, more preferably about 5%–10%).

For administration, the lyophilized powder is mixed (typically to yield a single dosage or multiple dosage formulation, about 100–500 mg, preferably 250 mg) with a suitable pharmaceutically-acceptable carrier, such as a phosphate buffered saline.

In other preferred embodiments in which the formulations are designed for parenteral administration, the compositions contain one or more sodium hydrogen phosphate or sodium, preferably sodium, salts of one or more sulfonamide compounds of formula I; a buffer, such as sodium or potassium phosphate, or citrate; and a sugar, such as sorbitol or dextrose. In a preferred embodiment described in detail herein, the formulations contain one or more sodium salts of the sulfonamide compounds of formula I; a sodium phosphate buffer; and dextrose. Dextrose may be added in the form of a sterile dextrose solution, which is readily available from suppliers known to those of skill in the art.

E. Methods of Identifying Peptides

The present invention relates to a method of identifying and evaluating peptides for their ability to induce an autoimmune response or to cause autoimmune disease. In particular, the invention relates to methods of (1) evaluating self-peptides for their potential involvement in autoimmune disease when the self epitope or autoantigen is unknown and (2) evaluating foreign peptides for their possible involvement in the aetiology of autoimmune disease. The invention also relates to specific peptides identified by the methods of the invention and representing self antigens implicated in pemphigus vulgaris.

The methods rely upon the development of amino acid sequence motifs to which potential self epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For consistency in this disclosure, but without limiting the invention in any way, these sequence motifs will be symbolized as strings of characters in which (a) a position which is restricted to a single residue will be represented by the one-letter abbreviation for that residue, (b) a position which is allowed to vary amongst a set of residues will be represented by a column of the one-letter abbreviations for those residues, and (c) a position which is allowed to vary amongst all amino acid residues will be represented by an "X." As an example only, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

In one aspect of the present invention, sequence motifs are developed by analysis of the binding domains or binding pockets of major histocompatibility complex HLA-DR proteins and/or the T cell receptor ("TCR") contact points of epitopes bound to MHC molecules. By providing a detailed structural analysis of the HLA-DR residues involved in forming the MHC binding pockets, one is enabled to make predictions of sequence motifs for binding to any of the HLA-DR proteins.

In another aspect of the present invention, sequence motifs developed by the methods disclosed herein may be used to identify self-peptide epitopes involved in an autoimmune response when the autoantigen is known or suspected.

In another aspect of the present invention, methods of identifying foreign peptide epitopes implicated in autoimmune disease are provided. These methods involve the use of MHC and/or TCR binding motifs to identify peptides derived from certain classes of organisms or pathogens which may initiate human autoimmune response. In this aspect, the motifs may be developed according to the methods of the present invention or by other means known in the art.

Using these sequence motifs as search, evaluation, or design criteria, one is enabled to identify classes of peptides which have a reasonable likelihood of binding to a particular MHC molecule and of interacting with a T cell receptor to induce T cell and/or autoimmune response. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a significant advance in the ability of one of ordinary skill in the art to evaluate particular peptides for potential involvement in autoimmune disease and to search computer databases of peptide sequences to identify self peptides which may be involved in autoimmune response. In addition, the use of MHC and/or TCR binding motifs to search limited databases for self peptides which may be implicated in the aetiology of autoimmune disease is a novel application of the concept of binding motifs.

Detailed examples of the practice of the present invention are presented below. The methods of the invention have now been used to identify the previously unknown self-peptide epitopes involved in the autoimmune disease pemphigus vulgaris.

Thus, in another embodiment, the invention provides these peptides, in isolated form, which may be used in various diagnostic and therapeutic methods and products alluded to below.

1. Identifying Self Epitopes Using Sequence Motifs

An ever increasing number of autoimmune diseases are now being associated with particular alleles of the MHC Class II HLA-DR locus. For most of these autoimmune diseases, the self epitope remains unknown. For some, however, a self protein involved in autoimmune response is known or suspected.

In one aspect of the present invention, a method is provided for identifying the self epitopes involved in autoimmune diseases associated with HLA-DR alleles. That is, by comparing human peptide sequences to the sequence motifs of the present invention, one is enabled to identify those peptides which have the highest likelihood of being the self epitopes involved in the disease.

The method may be applied to any of the autoimmune diseases for which an association with a particular HLA-DR allele is known and for which the amino acid residues forming the MHC binding pockets (or at least two of the major pockets) for that allele are known. In accordance with the method discussed herein, one may then develop one or more sequence motifs for the HLA-DR protein associated with the disease. Naturally, if the disease is associated with two or more alleles, motifs may be developed for the two or more HLA-DR proteins and, in particular, a consensus motif may be developed using the residues shared by each position of these motifs.

The sequence motif or motifs thus developed are then compared to appropriate sets of human peptide sequences. The human peptide sequences may include all known human sequences or may be limited in ways which will be obvious to one of ordinary skill in the art. For example, if the disease is restricted to particular tissues, the search may be limited to peptides found in those tissues. Conversely, peptides which are also found in unaffected tissues may be eliminated from the search pool. In the most extreme case, when the autoantigen is known or suspected but the particular epitope is unknown, the search may be limited to sequences within the autoantigen (see Example 1).

This method may be used to identify a set of peptides which match the motif and which are most likely to be self epitopes. By varying the number of positions restricted by the motifs, and/or the extent of restriction at each position, and/or the size of the search pool, the number of peptides in the set will, in all likelihood, also be varied. As noted above, at least two of the MHC contact positions (e.g., P1 and P4) should be restricted. Depending upon the number of peptides in the resultant set, a more or less restrictive motif may then be employed to reduce or expand the set. The desired size of the resultant set depends, of course, upon the subsequent intentions of the practitioner of this method.

Once a set of peptides has been identified, these peptides may optionally be screened for activity. The choice of such screens is at the discretion of the practitioner and beyond the scope of the present invention. Preferred screens, however, include in vitro tests for the ability to induce the proliferation of autoreactive T cells or to induce the secretion of lymphokines (cytokines) from these T cells or to induce other effector functions such as cytotoxicity. In some circumstances, human in vivo tests may be appropriate and in other circumstances animal models of the human disease may be available.

2. Identifying Foreign Epitopes Implicated in Human Autoimmune Disease

As noted in the background section, epidemiological evidence has suggested that various bacterial and viral pathogens may be implicated in human autoimmune diseases and the concept of molecular mimicry pervades the literature (reviewed by Oldstone, 1990). Prior attempts to identify particular foreign epitopes involved in human autoimmune disease, however, have depended upon direct sequence similarity to known human epitopes. The results have been disappointing and, to date, no pathogens or peptides derived from pathogens have been shown to be a primary cause of human autoimmune disease.

Thus, in another aspect of the present invention, a method of identifying foreign epitopes implicated in human autoimmune disease is provided. That is, for the first time a method of identifying such foreign epitopes is provided which employs sequence motifs to identify foreign peptides which have the highest likelihood of being involved in the aetiology of human autoimmune disease.

The method may be applied to any of the autoimmune diseases for which an association with a particular MHC protein is known and for which either (1) a sequence motif has been developed by prior art methods or (2) a sequence motif may be developed by the methods of the present invention. When the self epitope is known or suspected, TCR contact residues may be included in the motif. As before, one or more motifs may be employed and differently derived motifs may be combined to develop consensus motifs.

The sequence motif or motifs thus developed may then be compared to appropriate sets of peptide sequences derived from human pathogens. This is most conveniently accomplished using genetic databases widely available to those of skill in the art. In a most preferred embodiment, the search pool is limited in one or more of the following ways: (1) only sequences from human bacterial or viral pathogens are included; (2) sequences from the normal human intestinal flora (e.g., *E. coli* or other Enterobacteriaceae) are excluded; and (3) sequences from pathogens are included/excluded depending upon whether the geographical or epidemiological incidence of the pathogens are positively/negatively correlated with the incidence of the autoimmune disease in question.

This method may be used to identify a set of foreign peptides which match the motif and which are most likely to be involved in the human disease. As before, the number of peptides in the set can be varied by using more or less restrictive motifs and/or by varying the search pool. And, as before, the resultant set of peptides may subsequently be subjected to any of a variety of known screens for activity.

3. Self and Foreign Epitopes Identified by the Methods of the Present Invention.

As detailed in the examples below, the methods of the present invention have been employed to identify self epitopes of the desmoglein 3 protein implicated in pemphigus vulgaris.

Each peptide is fifteen residues in length, partly as a result of the computer database search program used (Genetics Computer Group program "Findpatterns") but also corresponding to the size of the cleft in MHC class II molecules.

The fifth position of each corresponds to the P1 residue of the antigen. Thus, the P2 to P11 residues which span the MHC Class II binding cleft correspond to the third through fifteenth residues of these sequences. The P1 to P9 residues which are important to MHC and TCR binding correspond to the fourth through thirteenth positions. The most important residues for MHC and TCR binding, P1 to P6 correspond to the fourth through tenth positions of these sequences.

The Dsg3 peptide having the amino acid sequence represented by SEQ ID NO: 1 corresponds to residues 186–204 of the human desmoglein 3 protein. This peptide is implicated as a self epitope in pemphigus vulgaris.

Each of these proteins has a variety of utilities and, therefore, in another aspect, the present invention provides each of these peptides in isolated form. In addition to the sequences shown in the Sequence Listing and Tables, the present invention also embraces the fragments of these peptides corresponding to the MHC binding domain. As will be obvious to one of ordinary skill in the art, however, any fragment of any of this peptide which includes at least the P1 and P4 or at least the P1 and P6 or at least the P4 and P6 residues may have utility and is intended to fall within the spirit and scope of the claims. In particular, longer peptides including these peptides or peptides including at least the MHC binding and TCR contact residues described above are contemplated as equivalents.

The manner of production of these peptides is inconsequential but they may be isolated and purified from their natural sources or they may be synthesized. Because of their relatively short length, it is presently contemplated that they should be produced by synthesis. Methods of isolation, purification and synthesis of such peptides are well known in the art and need not be recited herein.

The peptides of the present invention may be used for in vitro assays to aid in the diagnosis and classification of pemphigus vulgaris. For example, autoreactive T cells from patients with PV may be tested, as in the examples below or by other known assays, for reactivity with these peptides. The ability or inability of these peptides to cause proliferation of the T cells will, in the case of pemphigus, allow for a refinement of the diagnosis by particular desmoglein 3 epitopes. Immune response to these peptides prior to onset of disease may also be used as an indication of susceptibility or predisposition although care should be taken so as not to induce autoantigenic response.

F. Products and Methods using Peptides Identified by the Present Invention.

The present invention also provides products and methods using other peptides which may be identified by the methods of the present invention. These peptides, as well as those disclosed above, may be used in each of the following embodiments.

The peptides of the present invention may be used in the development of animal models by immunizing animals (e.g., mice, rabbits, non-human primates) with these peptides. Animals which not only develop a response to the peptide but which also develop an autoimmune disease corresponding to the human pathology will have obvious utility as models for the human disease. Animals which develop a response to the peptide without developing any corresponding autoimmune disease will have utility as subjects for experiments involving the selective depletion of T cells or other forms of desensitization or tolerization.

Importantly, these peptides and amino acid analogs of these peptides will have utility as therapeutic and diagnostic agents. The pathogens, viruses or bacteria from which they are derived will have utility as vaccinating agents. Some examples of the utility of these materials include the following.

The peptide may be administered in high doses to produce high dose tolerance. This process of tolerization is described in, for example, PCT patent application PCT/US93/08456 (International publication number WO 94/06828). Thus, in one set of embodiments, the invention provides for pharmaceutical preparations for use in tolerizing individuals to auto-antigens. The preparations may include a pharmaceutically acceptable carrier and an isolated human polypeptide which includes an amino acid sequence corresponding to a sequence motif for an HLA-DR protein which is associated with a human autoimmune disease. These polypeptides are capable of binding to the HLA-DR protein to form a complex which activates autoreactive T cells in subjects having an autoimmune disease. By using the peptides disclosed herein or identified by the methods of the invention, such pharmaceuticals can be used to combat autoimmune response. The use of such tolerization to human autoimmune diseases is known in the art and need not be elaborated upon here. Tolerizing doses of collagen for rheumatoid arthritis and myelin basic protein for multiple sclerosis have been used. The present invention therefore specifically does not embrace these proteins. Other peptides, however, may now be identified by the present methods and be similarly used to treat autoimmune disease.

In particular embodiments, such pharmaceutical preparations are provided in which the HLA-DR protein is HLA-DR4 protein and the autoimmune disease is pemphigus vulgaris. In addition, using Dsg3 motif #1 or motif #2, pharmaceuticals having peptides with this motif are provided. In most preferred embodiments, the pharmaceuticals include the polypeptide of SEQ ID NO: 1. Thus, methods of tolerizing an individual to a pemphigus vulgaris autoantigen are also provided.

In a similar set of embodiments, the invention provides for pharmaceutical preparations for use in tolerizing individuals to antigens of human pathogens which are implicated in human autoimmune disease. The preparations include a pharmaceutically acceptable carrier and an isolated human pathogen polypeptide which includes an amino acid sequence corresponding to a sequence motif for an HLA-DR protein which is associated with a human autoimmune disease. These polypeptides are capable of binding to the HLA-DR protein to form a complex which activates autoreactive T cells in subjects having an autoimmune disease. Thus, by tolerizing an individual to these antigens T cells which are cross-reactive with the self antigen will be rendered unresponsive or anergized and protection from the disease will be afforded.

In another set of embodiments, pharmaceuticals are provided for vaccination against a human pathogen implicated in the aetiology of autoimmune disease. These pharmaceutical preparations include a pharmaceutically acceptable carrier and an immunogenic preparation effective to immunize against a human pathogen. The human pathogen is one which in its native form includes a polypeptide having an amino acid sequence corresponding to a sequence motif for an HLA-DR protein which is associated with the autoimmune disease. These polypeptides are capable of binding to the HLA-DR protein to form a complex which activates T cells which become autoreactive and initiate the autoimmune disease. The preparations of the present invention specifically do not include such polypeptides but, rather, include other antigens from the pathogen. That is, a vaccine is produced which specifically does not include polypeptides which correspond to the sequence motifs for the HLA-DR protein and, if known, the TCR contacts of the self epitope. Because pathogens present a wide array of antigenic determinants one may eliminate those which correspond to the relevant sequence motif and produce a vaccine which is effective against the pathogen but which will not include peptides implicated in the autoimmune response.

Such vaccines, lacking peptides corresponding to the sequence motifs of the present invention, may be made in any convenient manner by one of ordinary skill in the art. For example, when producing an influenza vaccine, one may compare the peptide sequences of the influenza virus to sequence motifs developed according to the present invention. The vaccine may then be made excluding the proteins which have the motif sequences (e.g. by using a fragment of the virus) or recombinant techniques may be used to produce a virus in which the sequences corresponding to the motif are altered such that they do not match the motif. In preferred embodiments, the altered residues are the TCR contact residues and, in particular, a substitution which alters the charge of a TCR contact residue is preferred. Similar vaccines can be developed for bacterial pathogens using, for example, only portions of the bacterium (e.g. bacterial surface proteins or membrane associated proteins) which lack a motif associated with human autoimmune disease or, again, by genetically altering the vaccine bacteria so as to change residues.

The motifs which are considered in creating such vaccines may be chosen on any of several grounds. If the pathogen to which the vaccine is directed is associated with an autoimmune disease, a motif may be developed according to the methods described herein for an HLA-DR protein associated with the disease. If there is also a known or suspected autoantigen, the motif may include TCR contact residues of the self epitope. The pathogen's protein complement may then be compared to the motif and peptides corresponding to the motif may be omitted from the vaccine or may be altered by recombinant means to produce a vaccine free of such peptides. Alternatively, vaccines may be developed with particular populations in mind. For individuals suffering from or at risk of developing a particular autoimmune disease, special vaccines may be developed. In this case, the motif is again chosen on the basis of the HLA-DR protein associated with the autoimmune disease and, when known, the TCR contact residues of the self epitope.

In particular embodiments, such vaccine preparations are provided in which the HLA-DR protein is HLA-DR4 protein and the autoimmune disease is pemphigus vulgaris. And, in particular, vaccines are provided lacking a peptide corresponding to the Dsg3 motif #1 or motif #2 disclosed herein. Specific embodiments of the vaccines include vaccines lacking at least one of the peptides disclosed as SEQ ID NO: 1. Thus, methods of immunizing an individual against pathogens which may cause pemphigus vulgaris are also provided.

These peptides will also be useful in assessing which pathogen(s) may be important in a particular patient. For example, the T cells from one patient may proliferate in response to one or a few of these peptides, while those from another patient may proliferate in response to a different peptide or set of peptides. Analogs of the peptides may be synthesized in which one of the T cell receptor contact residues is substituted. Such analogs are not, however, limited to the substitution of these primary T cell receptor contact residues of to substitution by particular amino acids such as Ala. These peptide analogs may be used to anergize (inactivate) autoreactive T cells (see, for example, Sloan-Lancaster et al., 1993 and 1994) upon administration to autoimmune patients. The viruses or bacterial pathogens may be useful in immunization by selecting viral or bacterial strains that do not carry the mimicry epitope. Proteins from these pathogens other than those that carry the mimicry epitope may also be selected for immunization. This therapy may be useful in preventing re-infection and thus remissions of the disease or in preventing initial infections in particularly susceptible populations (the most obvious example of which is a disease-free identical twin of a patient).

EXAMPLES

Example 1

Identification of Self Epitopes of Pemphigus Vulgaris

As noted above, pemphigus vulgaris (PV) is, in different ethnic groups, associated either with a DR4 allele (DRB1*0402) or with a rare DQ1 allele (DQB1*05032); only a small fraction of PV patients have neither susceptibility gene (Ahmed et al., 1991; Ahmed et al., 1990; Scharf et al., 1988). The PV associated molecule has a negative charge (Glu) at the critical position β71; the neighboring position (β70) is also negatively charged. The DR4 subtype associated with PV is the only one that carries a negative charge at DRβ71 (a positive charge (Arg) is found at DRβ71 in the RA associated DR4 molecules). Although polymorphic, the P7 pocket residue DRβ67 (Leu/Ile) does not appear to be involved in peptide binding but probably acts as a TCR contact residue (Stem et al., 1994).

The charge of a polymorphic residue at DRβ71 could therefore account for susceptibility to two different autoimmune syndromes associated with structurally similar DR4 subtypes: DR4 alleles associated with susceptibility to rheumatoid arthritis have a positive charge at DRβ71 (Arg) while the DR4 allele associated with pemphigus vulgaris has a negative charge at DRβ71 (Glu). Peptides selective for either DR4 molecule may therefore differ significantly in their charge at P4: Peptides with a negative charge at P4 would be expected to bind to the RA associated molecules but not the pemphigus associated DR4 molecule; in contrast, a positive charge would be expected for the pemphigus peptide(s) at position 4. Due to the conserved nature of these molecules, other peptide anchor residues (P1 and P6) would not be expected to be different for these DR4 subtypes.

A sequence motif for selective binding to the HLA-DR DRB1*0402 protein was developed according to the method disclosed herein.

The β chain residues involved in forming the P1 pocket for this allele are β85 (Val), β86 (Val), β89 (Phe) and β90 (Thr). Thus, the presence of Val at β86 (instead of Gly as in DRB1*0101) suggests that the P1 position of the motif be restricted to V, L, I, M and F. Alanine might also have been included but was not in this example. The P6 pocket is formed in part by the β11 (Val) and β13 (His) of the DRB1*0402 protein. Relative to the DRB1*0101 allele, in which these residues are Leu and Phe respectively, the P6 pocket of the DRB1*0402 protein is somewhat larger and more polar. Thus, for the P6 position of the motif, S, T, N and V were allowed. Finally, the P4 pocket of this DR protein is formed in part by the residues β13 (His), β70 (Asp), β71 (Glu), β74 (Ala) and β78 (Tyr). As noted above, the two negatively charged residues as β70 and β71 create a preference for positively charged antigen residues and, therefore, the motif for the P4 position was restricted to K and R.

Thus, the sequence motif for the pemphigus vulgaris autoantigen was defined as:

|  | Position | | | | | | |
|---|---|---|---|---|---|---|---|
|  | P1 | P2 | P3 | P4 | P5 | P6 | |
| PV Motif #1 | L | N | S | K | I | A | (SEQ ID NO: 2) |
| PV Motif #2 | I | A | F | K | I | V | (SEQ ID NO: 3) |

Although the autoantigen for pemphigus vulgaris is known, the precise epitopes within the autoantigen have previously remained unknown. Using the method of the present invention, however, it has been possible to identify a small set of peptides which may serve as the autoantigenic determinants. The target antigen of pemphigus vulgaris is an epithelial adhesion molecule of the cadherin family, desmoglein 3 (Amagai et al., 1991). Desmoglein 3 mediates $Ca^{++}$ dependent adhesion between keratinocytes; the auto-antibodies interfere with cell adhesion with resulting blister formation (Takeichi, 1990). The auto-antibodies are thought to be pathogenic since a transient blistering disease is also seen in newborns of affected mothers due to transfer of maternal immunoglobulin to the fetus. Transfer of serum or desmoglein 3 specific antibodies to mice also results in acantholysis (Amagai et al., 1992).

The motifs of the present invention relating to the HLA-DR proteins can be taken one step further. In a different ethnic group PV is associated with a rare DQ1 subtype (DQB1*05032) that differs from the common DQ1 subtype only at position 57 of the DQβ chain (Sinha, et al., 1988). In the PV associated molecule DQβ57 is negatively charged (Asp) whereas in the common DQ1 subtype it is not. The same position on the DQβ chain has also been implicated in susceptibility to diabetes. In diabetes, however, the reverse is true: DQ2 and DQ8 molecules associated with susceptibility to diabetes do not have a negative charge at DQβ57 (Todd et al., 1987).

Based on these observations it becomes clear that two polymorphic positions in the MHC class II β chain (position 71 of DRβ and position 57 of DQβ) are critical for selective peptide binding and the development of autoimmunity. Based on the criteria described above, a diabetes linked peptide would be expected to have a negative charge at P9 since such a peptide would only bind to DQ molecules that do not have the same charge at DQβ57. In contrast, for the DQ1 associated cases of pemphigus, a peptide with a positive charge at P9 may be selective for the disease associated molecule which carries a negative charge at DQβ57. In the case of DR4 linked autoimmunity, the charge at peptide position 4 confers selectivity to the disease associated DR4 molecule: RA peptides have a negative charge at P4, PV peptides a positive charge at P4. Motifs for selective peptide binding may therefore prove to be tremendously useful in the identification of key epitopes that initiate human autoimmune diseases. This approach is expected to be useful not only for identifying peptides in PV, RA or diabetes but also for other autoimmune diseases where residues critical in peptide binding have been linked to disease susceptibility.

IV. Equivalents

Those skilled in the art will recognize, or be able to ascertain using no more than routine experimentation, many equivalents to the specific embodiments of the invention described herein. Such equivalents are intended to be encompassed by the following claims.

All of the references and publications cited herein are hereby incorporated in their entireties by reference.

EXAMPLES

The following examples are intended to further illustrate certain embodiments of the invention and are not intended to limit the scope of the invention.

Example I

Preparation of Segment I of the Peptide of SEQ ID NO: 1

Segment 1, Ac-Glu(OtBu)-Pro-Asn(Trt)-His(Trt)-Leu-Asn(Trt)-Ser(tBu)-Lys(Boc)-Ile-Ala-OH, (amino acids 1–10), is prepared by the solid phase peptide synthesis (SPPS) approach using an Fmoc-strategy. SPPS is based on the sequential addition of Fmoc-amino acid derivatives possessing appropriate side chain protection to an insoluble polymeric support. The base labile Fmoc-group is used for N-a-protection. The polymeric support employed in the synthesis of Segment 1 is the superacid labile HMPB resin, which is prepared with Fmoc-Ala coupled to the resin via its carboxy group. After removal of the Fmoc group with piperidine, the next Fmoc-amino acid is added using 2-(1 H-benzotriazole- 1-yl)-1,1,3,3-tetramethyluronium tetrafluoroborate (TBTU) as coupling reagent. The reaction is monitored by an in-process control trinitrobenzenesulfonic acid test (TNBS). When coupling of the Fmoc-amino acid is complete, excess amino acid derivatives and coupling reagents are removed by filtration. Finally, the resin is thoroughly washed using N-methypyrrolidone (NMP) and 2-propanol. This process is repeated sequentially until each of the desired amino acid derivatives have been coupled. Finally, the peptide is acetylated using acetic anhydride and pyridine. The resulting peptide is cleaved from the resin with dilute trifluoroacetic acid (TFA) to yield crude Segment 1. After purification by flash chromatography, Segment 1 is evaluated for purity.

Example II

Preparation of Segment 2 of the Peptide of SEQ ID NO: 1

Segment 2, H-Phe-Lys(Boc)-Ile-Val-Ser(tBu)-Gln(Trt)-Glu(tBu)-Pro-Ala-OtBu, (amino acids 11–19), is prepared by the solid phase peptide synthesis (SPPS) approach using an Fmoc-strategy. SPPS is based on the sequential addition of Fmoc- amino acid derivatives possessing appropriate side chain protection to an insoluble polymeric support. The base labile Fmoc-group is used for N-α-protection. The polymeric support employed in the synthesis of Segment 2 is the superacid labile HMPB resin, which is prepared with Fmoc-Ala coupled to the resin via its carboxy group. After removal of the Fmoc group with piperidine, the next Fmoc-amino acid is added using TBTU as coupling reagent. The reaction is monitored by an in-process control TNIBS test. When coupling of the Fmoc-amino acid is complete, excess amino acid derivatives and coupling reagents are removed by filtration. Finally, the resin is thoroughly washed using NMP and 2-propanol. This process is repeated sequentially until each of the desired amino acid derivatives have been coupled. The resulting peptide is cleaved from the resin with dilute TFA to yield the protected Fmoc-11–19-)H fragment. This peptide is treated with t-butyl-2,2,2-trichloracetimidate (TBTA) to protect the C-terminal carboxy group as the t-Butyl-ester(-OtBu). The esterified peptide is then purified by crystallization from dichloromethane/methanol. After purification by flash chromatography and drying, the Fmoc protecting group is cleaved. The amino-deprotected peptide is crystallized from water, recrystallized from d-isopropyl ether and dried to yield Segment 2. Segment 2 is evaluated for purity.

Example III

Manufacturing of PI-0824 Acetate from Segment 1 and Segment 2

There are three basic steps in the manufacture of the drug substance PI-0824 acetate from Segments 1 and 2. These steps are (1) coupling of the two segments, (2) de-protection and purification, and (3) ion-exchange chromatography to generate the acetate salt followed by filtration and drying of the finished peptide. These steps are summarized below.

1. Coupling of the Two Segments to Produce Ac-1-19-OtBu

The two segments are coupled in an N-methylpyrrolidone (NMP) solution using 1-hydroxy-7-azabenzotriazole (HOAt) and 1-ethyl-3-(3-dimethylaminopropyl) carbodiimide hydrochloride (EDCI) as coupling reagents. The completeness of the reaction is controlled by monitoring by using thin-layer chromatography (TLC). The product peptide is precipitated by addition into water while stirring. The precipitate is filtered, washed with water and acetonitrile, and dried. The purity is checked by HPLC.

2. De-Protection and Purification

The protecting groups are removed with TFA/H$_2$O. After precipitation in di-isopropyl ether, the peptide is filtered, washed with di-isopropyl ether and dried, giving the crude peptide×2 TFA.

The crude peptide×2 TFA is brought to the desired purity by means of preparative HPLC. The fractions are checked for purity by using HPLC as in process control, pooled and lyophilized to yield the pure peptide TFA-Salt. The lyophilized pure peptide TFA salt is checked for purity by HPLC.

3. Peptide Acetate

After replacement of the trifluoroacetate counterion by acetate using a strong basic ion-exchange resin in OH form (Merck ion exchanger III), the peptide is filtered (0.2 μm), and lyophilized in a clean room environment. The final drug substance, peptide acetate, is packaged and release tested by quality control.

Example IV

The peptide of the present invention is a portion of the human desmoglein 3 molecule (residues 186–204). The N-terminus of the peptide is acetylated and the peptide is isolated as the acetate salt. The molecular weight of the peptide acetate is 2,163 Daltons.

The peptide is prepared by solution phase coupling of two peptide fragments (Segment 1 and Segment 2) of ten and nine amino acids. These fragments are synthesized by standard Merrifield solid-phase peptide synthesis methods using the 9-fluorenylmethoxycarbonyl (Fmoc) strategy. After coupling of the two fragments and deprotection, the crude peptide is purified by reverse-phase high pressure liquid chromatography (HPLC). Release testing includes appearance, identity, peptide content and purity, solubility, acetic acid content, moisture content, residual organic solvents, and trifluoroacetic acid content.

The drug product is formulated by the addition of 3% mannitol and 20 mM sodium citrate/citric acid to obtain a solution having a total peptide content of 0.5%. The formulated peptide is filter-sterilized, aseptically filled and lyophilized. Each vial contains 50 mg of peptide acetate. The lyophilized product is reconstituted with water or 5% dextrose and or 0.01–5% surfactant for injection to give a final peptide concentration of 5 mg/mL and a pH of 6.3±0.5. Analysis of the composition to be administered to the patient includes appearance before and after reconstitution, moisture content, oxygen headspace, peptide content and purity, osmolality, pH, bacterial endotoxin and sterility.

Example V

A preferred embodiment of the present invention is a formulation of the polypeptide having increased stability. Stability data is reported for 2–8° C. (Table 1) and 30° C. (Table 2).

TABLE 1

| | | Stability at 2–8° C. | | | | |
|---|---|---|---|---|---|---|
| ASSAY | SPECIFICATION | 1 MONTH | 3 MONTHS | 6 MONTHS | 9 MONTHS | 12 MONTHS |
| Content | 4.5–5.5 mg/mL | 5.1 mg/mL | 5.1 mg/mL | 5.2 mg/mL | 5.2 mg/mL | 5.2 mg/mL |
| pH | 5.8–6.8 | 6.2 | 6.2 | 6.2 | 6.2 | N/A |
| Purity | ≧90% | 95.9% | 96.2% | 96.2% | 96.2% | 96.5% |
| Appearance Before reconstitution | White to off-white cake or powder | Pass | Pass | Pass | Pass | Pass |
| Appearance after reconstitution | Clear colorless solution | Pass | Pass | Pass | Pass | Pass |

TABLE 2

Stability at 30° C.

| ASSAY | SPECIFICATION | 1 MONTH | 3 MONTHS | 6 MONTHS | 9 MONTHS | 12 MONTHS |
|---|---|---|---|---|---|---|
| Content | 4.5–5.5 mg/mL | 5.2 mg/mL | 5.2 mg/mL | 5.1 mg/mL | 5.2 mg/mL | 5.1 mg/mL |
| pH | 5.8–6.8 | 6.2 | 6.2 | 6.3 | 6.2 | 6.2 |
| Purity | ≧90% | 96.1% | 96.0% | 95.8% | 96.0% | 96.1% |
| Appearance Before reconstitution | White to off-white cake or powder | Pass | Pass | Pass | Pass | Pass |
| Appearance after reconstitution | Clear colorless solution | Pass | Pass | Pass | Pass | Pass |

Example VI

The polypeptide of the present invention includes preferred embodiments. In one embodiment, the composition further comprises a pharmaceutically acceptable salt of the polypeptide. More preferably, the pharmaceutically acceptable salt is an acetate. In a further embodiment, the composition further comprises sugars, such as dextrose or mannitol. In a further embodiment, the composition further comprises buffers, such as sodium citrate, dehydrate or citric acid monohydrate. In a further embodiment, the composition further comprises stabilizers and/or bulking agents such as mannitol.

In one embodiment, the composition comprises a lyophilized polypeptide of SEQ ID NO: 1. In one embodiment, the lyophilized polypeptide has a reconstitution time of less than 15 minutes, more preferably, the reconstitution time is less than 10 minutes, more preferably, the reconstitution time is less than 5 minutes, and more preferably, the reconstitution time is less than 3 minutes.

In one embodiment, the purity of the peptide is greater than 90%, more preferably, the purity is greater than 93%, more preferably, the purity is greater than 95%, and more preferably, the purity is greater than 96%.

In one embodiment, the composition has bacterial endotoxin contamination of less than about 5 EU/mL, more preferably, the bacterial endotoxin contamination is less than about 3 EU/mL, more preferably, the bacterial endotoxin contamination is less than about 2 EU/mL, and more preferably, the bacterial endotoxin contamination is less than about 1.25 EU/mL.

More preferably, the composition of the present invention has the formulation as set forth in Table 3.

TABLE 3

Preferred composition formulation

| NAME OF INGREDIENT | AMOUNT PER VIAL | FUNCTION |
|---|---|---|
| Active Ingredients | | |
| Peptide (acetate) | 52.5 mg | Active Ingredient |
| Inactive Ingredients | | |
| Mannitol | 315 mg | Stabilizer/Bulking agent |
| Sodium citrate, dehydrate | 56.8 mg | Buffer |
| Citric acid, monohydrate | 3.5 mg | Buffer |
| Approximate weight of lyophilized cake | 428 mg | |

REFERENCES CITED

Ahmed, A. R., Yunis, E. J., Khatri, K., Wagner, R., Notani, G., Awdeh, Z., & Alper, C. A. (1990). Major histocompatibility complex haplotype studies in Ashkenazi Jewish patients with pemphigus vulgaris. *Proc. Natl. Acad. Sci.* (USA) 87:7658.

Ahmed, A. R., Wagner, R., Khatri, K., Notani, G., Awdeh, Z., and Yunis, E. J. (1991). Major histocompatibility complex haplotypes and class II genes in non-Jewish patients with pemphigus vulgaris. *Proc. Natl. Acad. Sci.* (USA) 88:5056.

Allegretta, M., Nicklas, J. A., Sriram, S. and Albertini, R. J. (1990). T cells responsive to myelin basic protein in patients with multiple sclerosis. *Science* 247:718–721.

Amagai, M., Klaus-Kovtun, V., & Stanley, J. R. (1991). Autoantibodies against a novel epithelial cadherin in pemphigus vulgaris, a disease of cell adhesion. *Cell* 67:869.

Amagai, M., Karpati, S., Prussick, R., Klaus-Kovtun, V., & Stanley, J. R. (1992). Autoantibodies against the amino-terminal cadherin-like binding domain of pemphigus vulgaris antigen are pathogenic. *J. Clin. Invest.* 90:919.

Brewerton, D. A., Hart, F. D., Caffrey, M., Nicholls, A., James, D. C. O., & Sturrock, R. D. (1973). Ankylosing spondylitis and HL-A 27. *Lancet* 1:904.

Brown, J. H., Jardetzky, T. S., Gorga, J. C., Stem, L. J., Urban, R. G., Strominger, J. L., & Wiley, D. C. (1993). Three-dimensional structure of the human class II histocompatibility antigen HLA-DR1. *Nature* 364:33.

Busch, R., Hill, C. M., Hayball, J. D., Lamb, J. R., Rothbard, J. B. (1991). Effect of a natural polymorphism at residue 86 of the HLA-DR .beta. chain on peptide binding. *J. Immunol.* 147:1292–1298.

Chicz, R. M., Urban, R. G., Gorga, J. C., Vignali, D. A. A., Lane, W. S., & Strominger, J. L. (1993). Specificity and promiscuity among naturally processed peptides bound to HLA-DR alleles. *J. Exp. Med.* 178:27.

Datta, A. K., Feighny, R. J., Pagano, J. S. (1980). Induction of Epstein-Barr virus-associated DNA polymerase by 12-O-tetradecanoylphorbol-13-acetate. *J. Biol. Chem.* 255: 5120–5125.

Epstein, M. A., Achong, B. G. (1977). Pathogenesis of infectious mononucleosis. *Lancet* 11:1270–1272.

Gregersen, P. K., Silver, J., Winchester, R. J. (1987). The shared epitope hypothesis. An approach to understanding the molecular genetics of susceptibility to rheumatoid arthritis. *Arthritis Rheum.* 30:1205.

Jardetzky, T. S., Lane, W. S., Robinson, R. A., Madden, D. R., & Wiley, D. C. (1991). Identification of self-peptides bound to purified HLA-B27. *Nature* 353:326.

Johnson, R. T., Griffin, D. E., Hirsch, J. S., Wolinsky, J. S., Rodenbeck, S., Lindo De Soriano, I. and Vaisberg, A.

(1984). Measles encephalomyelitis. Clinical and immunological studies. *N. Engl. J. Med.* 310:137–141.

Kaufman, D. L., Clare-Salzler, M., Tian, J., Forsthuber, T., Ting, G. S. P., Robinson, P., Atkinson, M. A., Sercarz, E. E., Tobin, A. J., and Lehmann, P. V. (1993). Spontaneous loss of T-cell tolerance to glutamic acid decarboxylase in murine insulin-dependent diabetes. *Nature* 366:69–72.

Kurtzke, J. F. (1985). "Epidemiology of multiple sclerosis" in Handbook of clinical neurology Eds. P. J. Vinken, G. W. Bruyn, H. L. Klawans and J. C. Koetsier. Amsterdam/New York, Elsevier Sci. 259–287.

Lanchbury, J. S., & Panayi, G. S. (1991). Genetics of RA: the HLA shared epitope hypothesis and its implications. *Br. J. Rheumatol.* 30(Suppl 2):6.

Lehmann, P. V., Forsthuber, T., Miller, A. and Sercarz, E. E. (1992). Spreading of T-cell autoimmunity to cryptic determinants of an autoantigen. *Nature* 358:155–157.

Madden, D. R., Gorga, J. C., Strominger, J. L., & Wiley, D. C. (1991). The structure of HLA-B27 reveals nonamer self-peptides bound in an extended conformation. *Nature* 353:321. Marsh, S. G. E. and Bodmer, J. G. (1992). HLA class II nucleotide sequences, 1992. *Human Immunol.* 35:1–17.

Martin, R., Jaraquemada, D., Flerlage, M., Richert, J., Whitaker, J., Long, E. O., McFarlin, D. E. and McFarland, H. F. (1990). Fine specificity and HLA restriction of myelin basic protein-specific cytotoxic T cell lines from multiple sclerosis patients and healthy individuals. *J. Immunol.* 145:540–548.

Oldstone, M. B. A. (1990). Molecular mimicry and autoimmune disease. *Cell* 50:819–820.

Olerup, O., Hillert, J., Fredrickson, S., Olsson, T., Kam-Hansen, S., Moeller, E., Carlsson, B. and Wallin, J. (1989). Primary chronic progressive and relapsing/remitting multiple sclerosis: Two immunogenetically distinct disease entities. *Proc. Natl. Acad. Sci. (USA)* 86:7113–7117.

Ota, K., Matsui, M., Milford, E. L., Mackin, G. A., Weiner, H. L. and Hafler, D. A. (1990). T-cell recognition of an immunodominant myelin basic protein epitope in multiple sclerosis. *Nature* 346:183–187.

Pette, M., Fujita, K., Wilkinson, D., Altmann, D. M., Trowsdale, J., Giegerich, G., Hinkkanen, A., Epplen, J. T. Kappos, L. and Wekerle, H. (1990). Myelin autoreactivity in multiple sclerosis: Recognition of myelin basic protein in the context of HLA-DR2 products by T lymphocytes of multiple sclerosis patients and healthy donors. *Proc. Natl. Acad. Sci. (USA)* 87:7968–7972.

Protti, M. P., Manfredi, A. A., Horton, R. M., Bellone, M., Conti-Tronconi, B. M. (1993). Myasthenia gravis: recognition of a human autoantigen at the molecular level. *Immunol. Today* 14:363.

Ray, C. G., Palmer, J. P., Crossley, J. R. and Williams, R. H. (1980). Coxsackie B virus antibody responses in juvenile-onset diabetes mellitus. *Clin. Endocrinol. (Oxt)* 12:375–378.

Rose, N. R., Wolfgram, L. J., Herskowitz, A. and Beisel, K. W. (1986). Postinfectious autoimmunity: Two distinct phases of coxsackie B3-induced myocarditis. *Ann. N.Y. Acad. Sci.* 475:146–156.

Rotschke, O., & Falk, K. (1991). Naturally-occurring peptide antigens derived from the MHC class-I-restricted processing pathway. *Immunol. Today* 12:447.

Scharf, S. J., Long, C. M., & Erlich, H. A. (1988). Sequence analysis of the HLA-DR.beta. and DQ.beta. loci from three pemphigus vulgaris patients. *Human Immunol.* 22:61.

Schlosstein, L., Terasaki, P. I., Bluestone, R., & Pearson, C. M. (1973). High association of an HL-A antigen, W27, with ankylosing spondylitis. *N. Engl. J. Med.* 288:704.

Schwarz, E., Freese, U. K., Gissman, L., Mayer, W., Roggenbuck, B., Stremlau, A., zur Hausen, H. (1985). Structure and transcription of human papillomavirus sequences in cervical carcinoma cells. *Nature* 314:111–114.

Sinha, A. A., Brautbar, C., Szafer, F., Friedmann, A., Tzfoni, E., Todd, J. A., Steinman, L., & McDevitt, H. O. (1988). A newly characterized HLA-DQ.beta. allele associated with pemphigus vulgaris. *Science* 239:1026.

Sloan-Lancaster, J., Evavold, B. D., and Allen, P. M. (1993) Induction of T-cell anergy by altered T-cell-receptor ligand on live antigen-presenting cells. *Nature* 363:156–159.

Sloan-Lancaster, J., Shaw, A. S., Rothbard, J. B. and Allen, P. M. (1994). Partial T cell signaling: Altered Phospho-.zeta. and lack of Zap70 recruitment in APL-induced T cell anergy. *Cell* 79:913–922.

Spielman, R. S., & Nathenson, N. (1982). The genetics of susceptibility to multiple sclerosis. *Epidemol. Rev.* 4:45.

Spruance, S. (1985). Pathogenesis of herpes simplex labialis: Experimental induction of lesions with UV light. *J. Clin. Microbiol.* 22:366–368.

Stern, L. J., Brown, J. H., Jardetzky, T. S., Urban, R., Strominger, J. L., & Wiley, D. C. (1994). Crystal structure of the human class II MHC protein HLA-DR1 complexed with an influenza virus peptide. *Nature* 368:215.

Takeichi, M. (1990). Cadherins: A molecular family important in selective cell-cell adhesion. *Ann. Rev. Biochem.* 59:237.

Tian, J., Lehmann, P. V. and Kaufman, D. L. (1994). T cell cross-reactivity between coxsackievairus and glutamate decarboxylase is associated with a murine diabetes susceptibility allele. *J. Exp. Med.* 180:1979–1984.

Tisch, R., Yang, X.-D., Singer, S. M., Liblau, R. S., Fugger, L., and McDevitt, H. O. (1993). Immune response to glutamic acid decarboxylase correlates with insulitis in non-obese diabetic mice. *Nature* 366:72–75.

Todd, J. A., Bell, J. I., & McDevitt, H. O. (1987). HLA-DQ.beta. gene contributes to susceptibility and resistance to insulin-dependent diabetes mellitus. *Nature* 329:599.

Tovey, M. G., Lenoir, G. and Begon-Lours, J. (1978). Activation of latent Epstein-Barr virus by antibody to human IgM. *Nature* 276:270–272.

Vogt, A. B., Kropshofer, H., Kalbacher, H., Kalbus, M., Rammensee, H.-G., Coligan, J. E. and Martin, R. (1994). Ligand motifs of HLA-DRB5*0101 and DRB1*1501 molecules delineated from self-peptides. *J. Immunol.* 151: 1665–1673.

Wucherpfennig, K. W., Sette, A., Southwood, S., Oseroff, C., Matsui, M., Strominger, J. L. and Hafler, D. A. (1994a). Structural requirements for binding of an immunodominant myelin basic protein peptide to DR2 isotypes and for its recognition by human T cell clones. *J. Exp. Med.* 179:279–290.

Wucherpfennig, K. W., Zhang, J., Witek, C., Matsui, M., Modabber, Y., Ota, K. and Hafler, D. A. (1994b). Clonal expansion and persistence of human T cells specific for an immunodominant myelin basic protein peptide. *J. Immunol.* 150:5581–5592.

Zamvil, S. S. and Steinman, L. (1990). The T lymphocyte in experimental allergic encephalomyelitis. *Annual Rev. Immunol.* 8:579–621.

Zhang, J., Markovic, S., Lacet, B., Raus, J., Weiner, H. L. and Hafler, D. A. (1994). Increased frequency of interleukin 2-responsive T cells specific for myelin basic protein and proteolipid protein in peripheral blood and cerebrospinal fluid of patients with multiple sclerosis. *J. Exp. Med.* 179:973–984.

We claim:

1. An isolated polypeptide consisting of the amino acid sequence of SEQ ID NO:1 or a pharmaceutically acceptable salt thereof.

2. A composition comprising a pharmaceutically acceptable carrier and the polypeptide of claim 1.

3. A composition comprising the pharmaceutically acceptable salt of the polypeptide of claim 1 and a pharmaceutically acceptable carrier.

4. The composition of claim 3, wherein the pharmaceutically acceptable salt is an acetate salt.

5. The composition of claim 2, further comprising a pharmaceutically acceptable additive selected from the group consisting of a sugar and a surfactant.

6. The composition of claim 2, further comprising buffers and bulking agents.

7. The composition of claim 5, wherein the sugar is dextrose or mannitol.

8. The composition of claim 7, wherein the composition is formulated for administration with about 5% dextrose.

9. The composition of claim 5, wherein the surfactant is selected from the group consisting of polysorbate 20 and polysorbate 80.

10. The composition of claim 9, wherein the composition is formulated with from about 0.01% to about 5% surfactant.

11. An isolated polypeptide wherein the polypeptide has an acetyl cap at its N-terminus, an amide cap at its C-terminus or both, and consists of the amino acid sequence of SEQ ID NO:1.

12. A composition comprising the polypeptide of claim 11 and a pharmaceutically acceptable carrier.

* * * * *